United States Patent
Moore et al.

(10) Patent No.: US 11,925,556 B2
(45) Date of Patent: Mar. 12, 2024

(54) PASSIVE ALIGNMENT OF COMMISSURES IN PROSTHETIC HEART VALVE IMPLANTATION

(71) Applicant: St. Jude Medical, Cardiology Division, Inc., St. Paul, MN (US)

(72) Inventors: Brandon Moore, St. Louis Park, MN (US); Daniel J. Klima, Andover, MN (US); Kristopher Henry Vietmeier, Monticello, MN (US); Jay Reimer, Saint Paul, MN (US); Peter J. Ness, Minneapolis, MN (US); Ryan Finn, St. Paul, MN (US); Jeffrey Paul LaPlante, Minneapolis, MN (US); Michael Shane Morrissey, St. Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 274 days.

(21) Appl. No.: 17/450,171

(22) Filed: Oct. 7, 2021

(65) Prior Publication Data

US 2022/0125584 A1   Apr. 28, 2022

Related U.S. Application Data

(60) Provisional application No. 63/105,382, filed on Oct. 26, 2020.

(51) Int. Cl.
*A61M 25/01* (2006.01)
*A61F 2/24* (2006.01)
*A61M 25/00* (2006.01)

(52) U.S. Cl.
CPC ....... *A61F 2/2436* (2013.01); *A61M 25/0074* (2013.01); *A61M 25/0113* (2013.01);
(Continued)

(58) Field of Classification Search
CPC ............. A61F 2/2436; A61M 25/0125; A61M 25/0069
See application file for complete search history.

(56) References Cited

U.S. PATENT DOCUMENTS

| 3,205,863 A | 9/1965 | Kent |
| 7,399,315 B2 | 7/2008 | Iobbi |

(Continued)

FOREIGN PATENT DOCUMENTS

| EP | 3111889 B1 | 11/2019 |
| WO | 2011035327 A1 | 3/2011 |

(Continued)

OTHER PUBLICATIONS

Extended European Search Report issued in Appln. No. 21204507.4 dated Mar. 14, 2022 (3 pages).

*Primary Examiner* — Rebecca S Preston
(74) *Attorney, Agent, or Firm* — SLEMAN & LUND LLP

(57) ABSTRACT

A delivery device for a collapsible prosthetic heart valve includes an inner shaft, an outer shaft, and a distal sheath. The distal sheath may be disposed distal to the outer shaft and about a portion of the inner shaft to form a compartment with the inner shaft. The compartment may be sized to receive the prosthetic heart valve. The inner shaft and the distal sheath may be movable relative to one another. A spine may extend along the outer shaft, the spine biasing the outer shaft so that the outer shaft tends to bend in a pre-determined direction.

12 Claims, 11 Drawing Sheets

(52) U.S. Cl.
CPC . *A61M 25/0125* (2013.01); *A61F 2210/0014* (2013.01); *A61F 2230/0006* (2013.01); *A61F 2230/006* (2013.01); *A61M 25/0152* (2013.01)

(56) References Cited

U.S. PATENT DOCUMENTS

| | | |
|---|---|---|
| 8,052,750 B2 | 11/2011 | Tuval et al. |
| 8,512,398 B2 | 8/2013 | Alkhatib |
| 9,532,868 B2 | 1/2017 | Braido |
| 9,545,306 B2 | 1/2017 | Tabor |
| 2005/0288777 A1 | 12/2005 | Rhee et al. |
| 2007/0260263 A1* | 11/2007 | Case ............... A61M 25/01 623/2.11 |
| 2016/0296324 A1 | 10/2016 | Bapat et al. |
| 2018/0028177 A1 | 2/2018 | Van Oepen |
| 2018/0125643 A1 | 5/2018 | Bourang et al. |
| 2018/0153693 A1 | 6/2018 | Copeland et al. |
| 2018/0303644 A1* | 10/2018 | Rothstock ............ A61F 2/2433 |
| 2021/0068956 A1 | 3/2021 | Gale et al. |
| 2021/0169645 A1 | 6/2021 | Dale et al. |
| 2022/0142777 A1* | 5/2022 | Scheinblum ......... A61F 2/2418 |

FOREIGN PATENT DOCUMENTS

| | | |
|---|---|---|
| WO | 2015061463 A1 | 4/2015 |
| WO | 2017123802 A1 | 7/2017 |

\* cited by examiner

PASSIVE ALIGNMENT OF COMMISSURES IN PROSTHETIC HEART VALVE IMPLANTATION

CROSS-REFERENCE TO RELATED APPLICATIONS

This application claims the benefit of the filing date of U.S. Provisional Patent Application No. 63/105,382, filed Oct. 26, 2020, the disclosure of which is hereby incorporated by reference herein.

BACKGROUND OF THE DISCLOSURE

The present disclosure relates to systems and methods for aligning commissures of prosthetic heart valves with native commissures of the heart valve being replaced by the prosthetic heart valve.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

When a prosthetic heart valve is implanted into a native heart valve, it may be desirable for the commissures of the prosthetic heart valve (e.g. the areas at which a side of one prosthetic heart valve leaflet meet with a side of an adjacent prosthetic heart valve leaflet) to rotationally align with the native commissures of the native heart valve. Such alignment may help reduce the risk of coronary obstruction, and it may be generally desirable for the prosthetic valve to mimic the native valve anatomy as closely as possible. When implanting prosthetic heart valves surgically (i.e. through an open heart, open chest procedure), there is typically good visualization of the operative field, which makes alignment of the prosthetic commissures with the native commissures relatively easy. However, in transcatheter procedures, the entire surgical field is not capable of visualization by the naked eye of the surgeon. For example, deployment of the prosthetic heart valve in a transcatheter procedure is frequently performed under fluoroscopic imaging. Also, the prosthetic heart valve is typically positioned at one end of a delivery device whereas the surgeon is manipulating the opposite end of the delivery device. This can make it significantly more difficult to align the commissures of the prosthetic heart valve with the native valve commissures during a transcatheter heart valve replacement procedure compared to a surgical heart valve replacement procedure. Thus, it would be desirable for systems and methods to help assist with aligning commissures of a prosthetic heart valve with native heart valve commissures, particularly for transcatheter implantation systems.

SUMMARY OF THE DISCLOSURE

According to one aspect of the disclosure, a delivery device for a collapsible prosthetic heart valve includes an inner shaft, an outer shaft, and a distal sheath. The distal sheath may be disposed distal to the outer shaft and about a portion of the inner shaft to form a compartment with the inner shaft. The compartment may be sized to receive the prosthetic heart valve. The inner shaft and the distal sheath may be movable relative to one another. A spine may extend along the outer shaft, the spine biasing the outer shaft so that the outer shaft tends to bend in a pre-determined direction.

According to another aspect of the disclosure, a method of implanting a prosthetic heart valve into a native aortic valve of a patient includes loading the prosthetic heart valve into a distal sheath of a delivery device in a collapsed condition, the prosthetic heart valve having three prosthetic commissures. The distal sheath of the delivery device may be advanced through an aortic arch of the patient so that an outer shaft of the delivery device includes a bend having an outer radius and an inner radius, one of the three prosthetic commissure confronting the outer radius of the bend during the advancing. The distal sheath may be continued to be advanced until the distal sheath is adjacent the native aortic valve and the distal sheath is positioned adjacent a native commissure between a right coronary cusp and non-coronary cusp of the patient. The distal sheath may be retraced and the prosthetic heart valve may expand so that the one of the three prosthetic commissure is positioned in rotational alignment with the native commissure.

According to a further aspect of the disclosure, a delivery device for a collapsible prosthetic heart valve includes an inner shaft, an outer shaft, and a distal sheath. The distal sheath may be disposed distal to the outer shaft and about a portion of the inner shaft to form a compartment with the inner shaft, the compartment being sized to receive the prosthetic heart valve. The inner shaft and the distal sheath may be movable relative to one another, the outer shaft and the distal sheath sharing a central longitudinal axis. The outer shaft may be joined to the distal sheath via a joint so that the distal sheath is capable of rotation about the central longitudinal axis while the outer shaft remains static relative to the central longitudinal axis.

DETAILED DESCRIPTION OF THE DISCLOSURE

As used herein in connection with prosthetic heart valves, the term "inflow end" refers to the end of the heart valve through which blood first flows when implanted in an intended position and orientation, while the term "outflow end" refers to the opposite end, through which blood last flows when the prosthetic heart valve is implanted in the intended position and orientation. When used in connection with devices for delivering a prosthetic heart valve into a patient, the terms "proximal" and "distal" are to be taken as relative to the user of the delivery devices. In other words, in this context, "proximal" is to be understood as relatively close to the user of the delivery device, and "distal" is to be understood as relatively farther away from the user of the delivery device.

Figure 1:
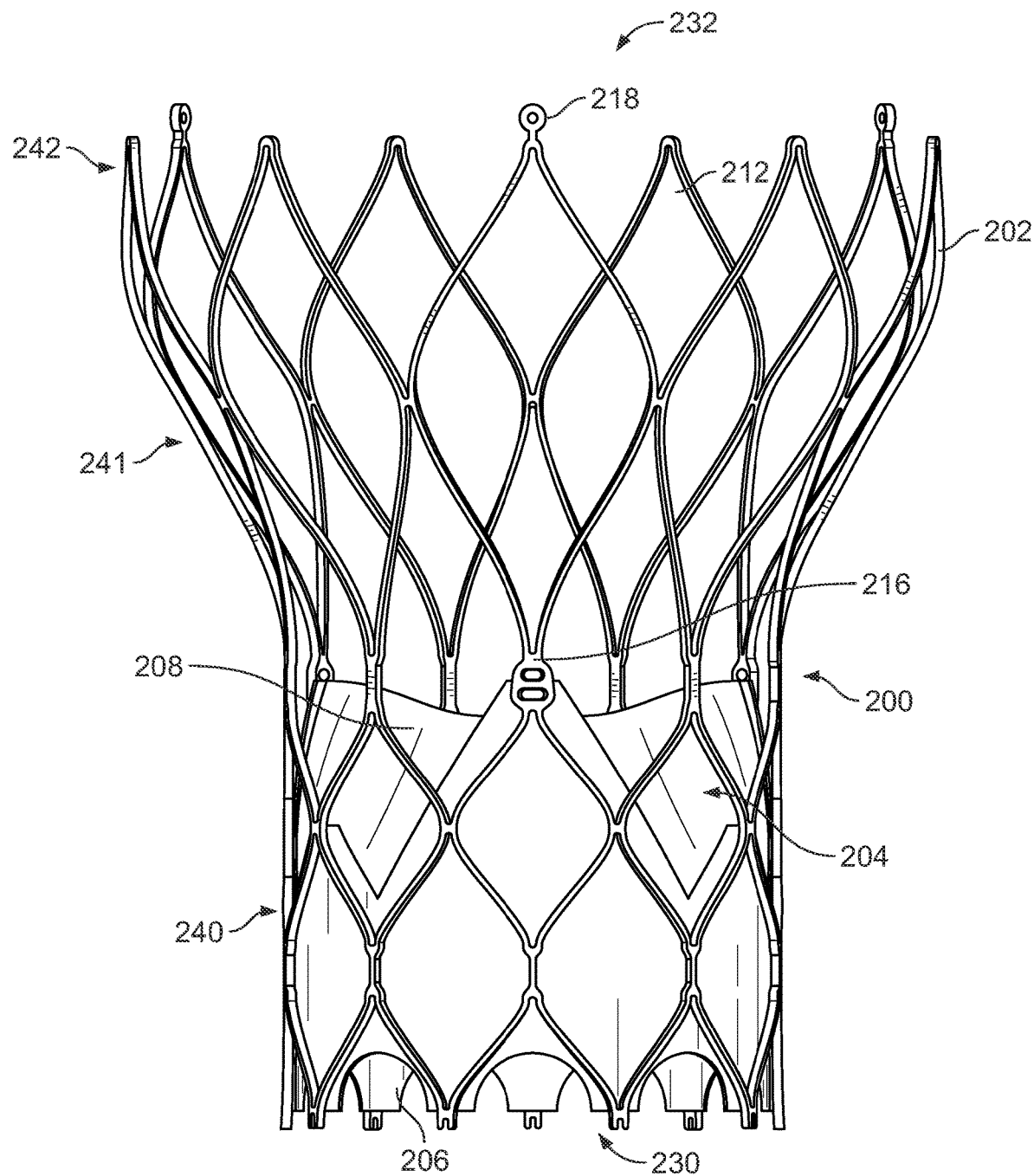
FIG. 1 is a side elevational view of a collapsible prosthetic heart valve in an expanded condition, showing the valve assembly attached to the stent.

FIG. 1 shows a collapsible prosthetic heart valve 200. The prosthetic heart valve 200 is designed to replace the function of a native aortic valve of a patient, although it should be understood that the concepts described herein may be applicable to the replacement of any native heart valve, including the mitral, tricuspid, or pulmonary heart valves. As discussed in detail below, the prosthetic heart valve has an expanded condition, shown in FIG. 1, and a collapsed condition.

Prosthetic heart valve 200 includes a collapsible and expandable stent 202 which may be formed from any biocompatible material, such as metals, metal alloys, synthetic polymers or biopolymers capable of functioning as a stent. Stent 202 extends from an inflow or annulus end 230 to an outflow or aortic end 232, and includes an annulus section 240 adjacent the inflow end and an aortic section 242 adjacent the outflow end. The annulus section 240 has a relatively small cross-section in the expanded condition, while the aortic section 242 has a relatively large cross-section in the expanded condition. Preferably, annulus section 240 is in the form of a cylinder having a substantially constant diameter along its length. A transition section 241 may taper outwardly from the annulus section 240 to the aortic section 242. Each of the sections of the stent 202 includes a plurality of cells 212 connected to one another in one or more annular rows around the stent. For example, as shown in FIG. 1, the annulus section 240 may have two annular rows of complete cells 212 and the aortic section 242 and transition section 241 may each have one or more annular rows of partial cells 212. The cells 212 in the aortic section 242 may be larger than the cells 212 in the annulus section 240. The larger cells in the aortic section 242 better enable the prosthetic valve 200 to be positioned without the stent structure interfering with blood flow to the coronary arteries.

Stent 202 may include one or more retaining elements 218 at the outflow end 232 thereof, the retaining elements being sized and shaped to cooperate with female retaining structures provided on the deployment device. The engagement of retaining elements 218 with the female retaining structures on the deployment device helps maintain prosthetic heart valve 200 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and during deployment.

The prosthetic heart valve 200 includes a valve assembly 204 positioned in the annulus section 240. Valve assembly 204 includes a cuff 206 and a plurality of leaflets 208 which collectively function as a one-way valve. The commissure between adjacent leaflets 208 may be connected to commissure features 216 on stent 202. Prosthetic heart valve 200 is shown in FIG. 1 with three leaflets 208, as well as three commissure features 216. As can be seen in FIG. 1, the commissure features 216 may lie at the intersection of four cells 212, two of the cells being adjacent one another in the same annular row, and the other two cells being in different annular rows and lying in end-to-end relationship. Preferably, commissure features 216 are positioned entirely within annulus section 240 or at the juncture of annulus section 240 and transition section 241. Commissure features 216 may include one or more eyelets which facilitate the suturing of the leaflet commissure to the stent. However, it will be appreciated that the prosthetic heart valves may have a greater or lesser number of leaflets and commissure features. For example, a prosthetic mitral valve may include two prosthetic leaflets with two commissures. Additionally, although cuff 206 is shown in FIG. 1 as being disposed on the luminal surface of annulus section 240, it is contemplated that the cuff may be disposed on the abluminal surface of annulus section 240, or may cover all or part of either or both of the luminal and abluminal surfaces of annulus section 240. Both the cuff 206 and the leaflets 208 may be wholly or partly formed of any suitable biological material or polymer.

In operation, a prosthetic heart valve, including the prosthetic heart valve described above, may be used to replace a native heart valve, such as the aortic valve, a surgical heart valve or a heart valve that has undergone a surgical procedure. The prosthetic heart valve may be delivered to the desired site (e.g., near a native aortic annulus) using any suitable delivery device, including the delivery devices described in detail below. During delivery, the prosthetic heart valve is disposed inside the delivery device in the collapsed condition. The delivery device may be introduced into a patient using a transfemoral, transapical or transseptal approach, although any transcatheter approach may suitable. Once the delivery device has reached the target site, the user may deploy the prosthetic heart valve. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction.

In a prosthetic aortic heart valve, the valve assembly may be spaced from the outflow or aortic end of the stent by a distance that enables deployment of the heart valve by an amount sufficient for the valve leaflets of the prosthetic valve to operate as intended, while the outflow end of the stent remains captured by the delivery device. More particularly, the inflow or annulus end of the prosthetic heart valve may be deployed first, while the aortic or outflow end of the prosthetic heart valve remains at least partially covered by a distal sheath of the delivery device. The annulus portion of the prosthetic heart valve may be deployed so that the entirety of the valve leaflets, up to and including the commissures, is deployed and fully operational. By deploying the prosthetic heart valve in this manner, the user can determine whether the valve leaflets are properly positioned relative to the native valve annulus, and whether the valve is functioning properly. If the user determines that the positioning and operation of the valve are acceptable, the remainder of the valve may be deployed. However, if it is determined that the leaflet position is improper or that the valve is not functioning properly, the user may resheath the valve and either reposition it for redeployment, or remove it entirely from the patient.

As is shown in FIG. 1, in one embodiment the entirety of valve assembly 204, including the leaflet commissures, is positioned in the annulus section 240 of stent 202. When opened, the leaflets may extend further into the transition section 241 or may be designed such that they remain substantially completely within the annulus section. That is, substantially the entirety of valve assembly 204 is positioned between the inflow end 230 of stent 202 and the commissure features 216, and none of the valve assembly 204 is positioned between commissure features 216 and the outflow end 232 of the stent. Indeed, in some embodiments, the valve can be designed such that, upon partial deployment, the commissure features are fully exposed, oriented generally parallel to the direction of blood flow, and at or near their actual radially expanded positions (but not necessarily their eventual positions relative to the annulus), such that the leaflets can operate substantially as they would when the valve is fully deployed, even though enough of the stent is still retained within the delivery device or sheath to permit resheathing.

In one arrangement, the distance between commissure features 216 and the outflow end 232 of stent 202 will be about two-thirds of the length of the stent from the inflow end 230 to the outflow end. This structural arrangement may provide advantages in the deployment of prosthetic valve 200 as will be discussed in more detail with reference to FIGS. 2A and 2B. By having the entirety of valve assembly 204 positioned within annulus section 240, and by having a sufficient distance between commissure features 216 and the distal end 232 of stent 202, the valve assembly and commissures will not impede blood flow into the coronary arteries and will not interfere with access thereto during cardiac intervention, such as angiography, annuloplasty or stent placement.

Further, it is possible to partially deploy prosthetic valve 200 so that the valve assembly 204 thereof is able to fully function in its intended position in the native valve annulus, while a sufficient amount of the aortic section 242 is retained within the delivery device should resheathing become necessary. In other words, the user may withdraw the distal sheath of the delivery device to gradually expose prosthetic valve 200, beginning at the inflow end 230. Continued withdrawal of the distal sheath will expose a greater extent of the prosthetic valve until the entire annulus section 240 and valve assembly 204 have been exposed. Upon exposure, these portions of the prosthetic valve will expand into engagement with the native valve annulus, entrapping the native valves, except for a small portion immediately adjacent the free end of the distal sheath which will be constrained by the distal sheath from fully expanding.

However, once the distal sheath has been withdrawn to expose a sufficient portion of the aortic section 242, the annulus section 240 will be able to fully expand and valve assembly 204 will be able to function in the same manner as if the entirety of prosthetic valve 200 had been deployed. At this juncture, it will be possible for the user to ascertain whether annulus section 240 and valve assembly 204 have been properly positioned relative to the native valve annulus, and whether the valve assembly is functioning properly.

If the position and operation of valve assembly 204 are acceptable, the distal sheath may be withdrawn further to deploy the remainder of prosthetic valve 200. On the other hand, if the positioning or operation of valve assembly 204 are unacceptable, the user may advance the distal sheath to resheathe the prosthetic valve, reposition the valve and initiate the deployment procedure anew. And if it is determined that the valve is not functioning properly, it can be withdrawn from the patient and a new valve introduced.

Figure 2A:
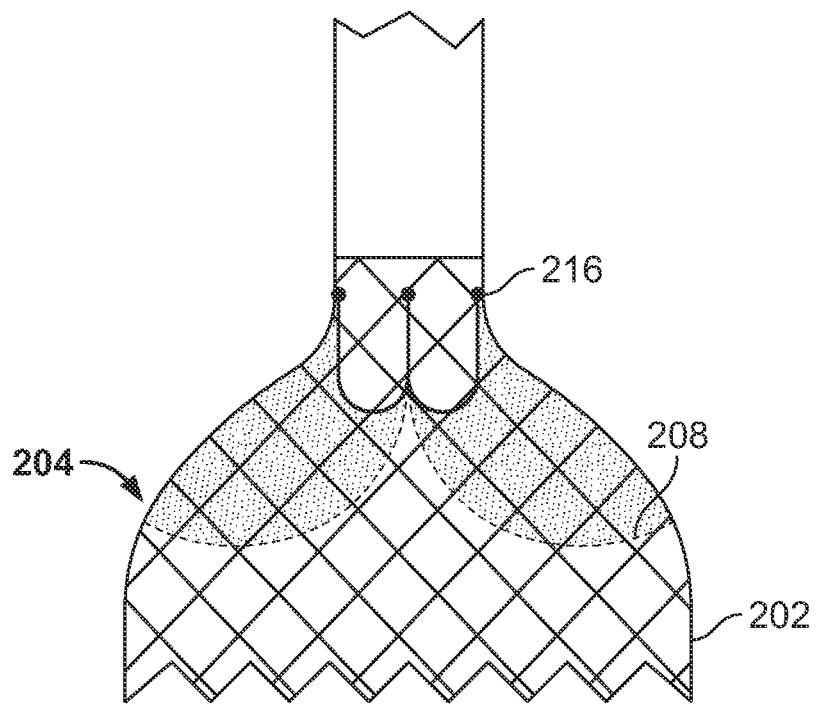
FIG. 2A is a highly schematic side elevational view showing partial deployment of a collapsible prosthetic heart valve with high placement.
Figure 2B:
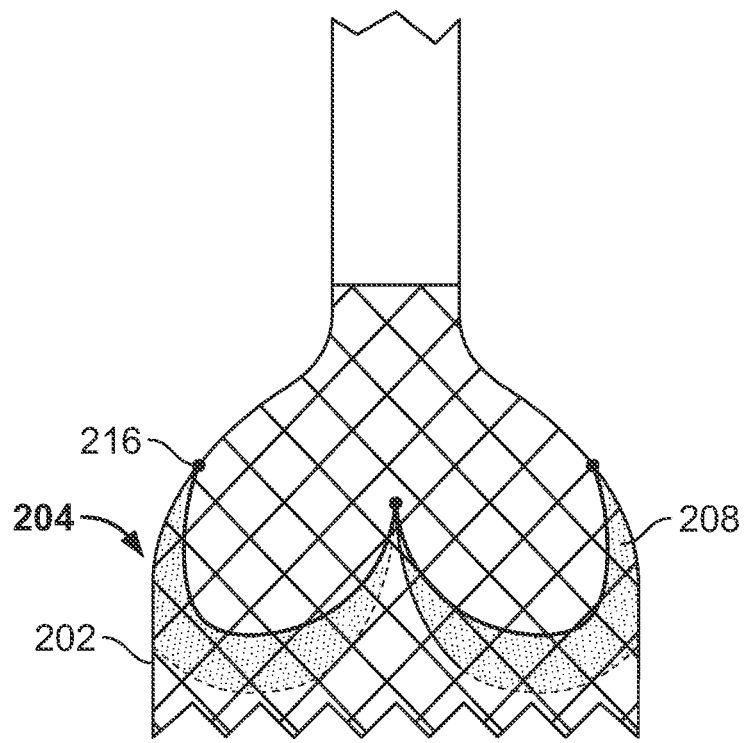
FIG. 2B is a highly schematic side elevational view showing partial deployment of a collapsible prosthetic heart valve with low placement.

It will be appreciated from the foregoing that the placement of the leaflets 208 within the stent 202 can affect the valve functioning during partial deployment. FIG. 2A illustrates a valve assembly 204 with high placement, while FIG. 2B illustrates a valve assembly with low placement. As used herein, the phrase "high placement" of a valve assembly refers to locating the valve assembly within the transition section 241 of the stent 202, or within the portion of the annulus section 240 closest to the transition section. The phrase "low placement" of a valve assembly refers to locating the valve assembly closer to the inflow end 230 of the stent 202 and entirely within the annulus section 240 thereof, such that the leaflets 208 are substantially disposed within the annulus section.

As seen in FIG. 2A, during partial deployment the annulus end of the heart valve 200 is unsheathed and allowed to expand. The outflow end 232, including the aortic section 242, remains partially sheathed and coupled to the delivery device. It should be appreciated that high placement of valve assembly 204 will cause the valve assembly to not be fully deployed when heart valve 200 is only partially deployed, thereby affecting leaflet function. Specifically, since the commissure features 216 are located closer to or within the transition section 241, they do not reach their fully expanded positions. As such, the leaflets 208 remain partially closed at this stage of deployment. Because of the location of the commissure features 216 and the leaflets 208, the valve assembly 204 cannot be tested during partial deployment. Instead, the user must unsheathe a portion of the aortic section 242 as well, which may pose problems if the valve assembly 204 is to be resheathed and redeployed.

In contrast to the prosthetic heart valve of FIG. 2A, the heart valve 200 of FIG. 2B exhibits low placement of the valve assembly 204 within the annulus section 240. Low placement of the valve assembly 204 enables the valve assembly to fully deploy when heart valve 200 is only partially deployed. As such, leaflets 208 reach their fully expanded and open positions during partial deployment and are able to function near normally, enabling a better assessment of the valve's functioning and final placement within the actual anatomy. Thus, if it appears that the valve needs to be moved, the heart valve 200 may be easily resheathed and repositioned. This concept is beneficial when dealing with less than ideal anatomical configurations.

The shape of the stent 202 during partial deployment will also affect the valve 204. If the stent shape is such that, while still partially retained by the sheath, it cannot open sufficiently to allow operation of the valve, it may not be possible to fully assess the operation of the valve in its intended placement position. Moreover, the height of the valve commissure features 216 relative to the inflow end 230 of the valve will affect the valve function. The lower the commissure features 216, meaning the closer to the inflow end 230, the more they will expand outwardly and the valve leaflets will be able to open during partial deployment, creating a flow passageway through the leaflets which approaches that of a fully deployed valve.

A transfemoral or transapical delivery device may be used to partially deploy the prosthetic heart valve such that an assessment may be made regarding flow through the valve and adequacy of coaptation. If, after the annulus section is unsheathed and the valve is tested, it is found that the valve needs to be repositioned, the annulus section may be resheathed and the valve redeployed as necessary.

Figure 3:
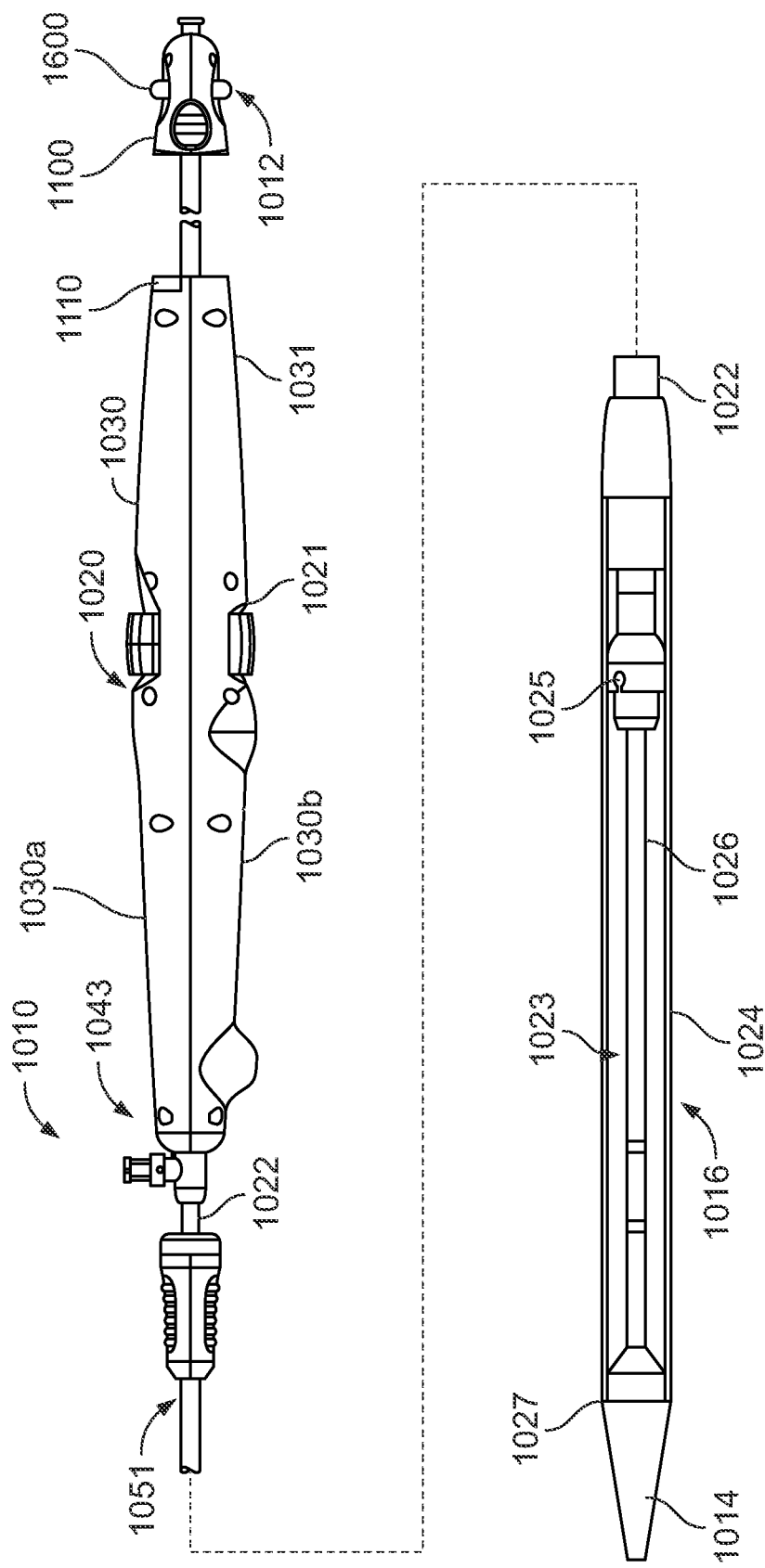
FIG. 3 is side view of an operating handle for a transfemoral delivery device for a collapsible prosthetic heart valve, shown with a side elevational view of the distal portion of a transfemoral catheter assembly.

Turning now to FIG. 3, an exemplary transfemoral delivery device 1010 for a collapsible prosthetic heart valve (or other types of self-expanding collapsible stents) has a catheter assembly 1016 for delivering the heart valve to and deploying the heart valve at a target location, and an operating handle 1020 for controlling deployment of the valve from the catheter assembly. The delivery device 1010 extends from a proximal end 1012 to a distal tip 1014. The catheter assembly 1016 is adapted to receive a collapsible prosthetic heart valve (not shown) in a compartment 1023 defined around an inner shaft 1026 and covered by a distal sheath 1024. The inner shaft 1026 extends through the operating handle 1020 to the distal tip 1014 of the delivery device, and includes a retainer 1025 affixed thereto at a spaced distance from distal tip 1014 and adapted to hold a collapsible prosthetic valve in the compartment 1023.

The distal sheath 1024 surrounds the inner shaft 1026 and is slidable relative to the inner shaft such that it can selectively cover or uncover the compartment 1023. The distal sheath 1024 is affixed at its proximal end to an outer shaft 1022, the proximal end of which is connected to the operating handle 1020. The distal end 1027 of the distal sheath 1024 abuts the distal tip 1014 when the distal sheath fully covers the compartment 1023, and is spaced apart from the distal tip 1014 when the compartment 1023 is at least partially uncovered.

The operating handle 1020 is adapted to control deployment of a prosthetic valve located in the compartment 1023 by permitting a user to selectively slide the outer shaft 1022 proximally or distally relative to the inner shaft 1026, or to slide the inner shaft 1026 relative to the outer shaft 1022, thereby respectively uncovering or covering the compartment with the distal sheath 1024. Operating handle 1020 includes frame 1030 which extends from a proximal end 1031 to a distal end and includes a top frame portion 1030a and a bottom frame portion 1030b. The proximal end of the inner shaft 1026 is coupled to a hub 1100, and the proximal end of the outer shaft 1022 is affixed to a carriage assembly within the frame 1030 that is slidable within the operating handle along a longitudinal axis of the frame 1030, such that a user can selectively slide the outer shaft relative to the inner shaft by sliding the carriage assembly relative to the frame. Alternatively, inner shaft 1026 may be actuated via hub 1100 to cover or uncover the compartment, for example for rapid covering or uncovering of the compartment 1023. Optionally, a stability sheath 1051 is disposed over some or all of outer shaft 1022. The stability sheath 1051 may be attached to the outer shaft 1022 or may be unattached. Additionally, stability sheath 1051 may be disposed over a majority of outer shaft 1022 or over a minority of the outer shaft (e.g., over 49% or less, over 33%, etc.). Optionally, stability sheath 1051 may be more rigid than outer shaft 1022.

Additionally, hub 1100 may include a pair of buttons, each attached to a clip. These clips on hub 1100 may mate with voids on frame 1030 to ensure that the hub and the frame are securely coupled together. Optionally, hub 1100 may also include a wheel 1600 which may assist in reducing strain in the distal sheath 1024 when loading the prosthetic heart valve into the delivery device 1010.

A first mechanism for covering and uncovering the compartment 1023 will be referred to as a "fine" technique as covering and uncovering occurs slowly with a high degree of precision. The "fine" movement may be provided by rotating a deployment wheel or actuator 1021, which may cause the carriage to pull or push the outer sheath 1022 (and thus the distal sheath 1024) proximally or distally. The second mechanism for covering and uncovering the compartment 1023 may be referred to as a "coarse" technique, by pulling or pushing the hub 1100 as described above. The "coarse" technique may be particularly suited for use when a prosthetic heart valve is not positioned within the compartment 1023. The delivery device may also include a resheathing lock 1043, which may restrict motion of the distal sheath 1024 once full deployment of the prosthetic heart valve is imminent. The resheathing lock 1043 may be disengaged when the desired position of the prosthetic heart valve is confirmed, so that the distal sheath 1024 may be further retracted to full release the prosthetic heart valve. In other words, the resheathing lock 1043 may help prevent unintentional or premature complete deployment of the prosthetic heart valve. Additional features of the delivery device 1010, for example including the function of wheel 1600, are described in greater detail in U.S. Patent Publication No. 2018/0153693, the disclosure of which is hereby incorporated by reference herein.

As noted above, it is often desirable for the commissures of the prosthetic heart valve to align rotationally with the commissures of the native heart valve upon deployment and/or implantation of the prosthetic heart valve into the native heart valve. Generally, such alignment may be approached from an active or passive standpoint. Active alignment generally refers to the inclusion of some mechanism that the user can activate or otherwise actively use to increase the likelihood of commissure alignment, for example by actively rotating the prosthetic heart valve until the prosthetic commissures are rotationally aligned with the native commissures. Passive alignment, on the other hand, generally referrers to the inclusion of some mechanism or design that allows the prosthetic heart valve commissures to rotationally align with the native heart valve commissures without the user actively inducing such alignment. The description below generally focuses on passive commissure-to-commissure alignment mechanisms and designs. It should be understood that although various passive commissure-to-commissure alignment mechanisms are described below, more than one of the mechanisms may be provided in a single system.

Certain embodiments below focus on features that exploit the geometry of the aortic arch and/or the aortic root. Features that exploit the geometry of the aortic arch may be particularly useful when transfemoral retrograde delivery is employed, since transfemoral delivery typically includes advancing the prosthetic heart valve and delivery device up and around the aortic arch, and then into or adjacent the native aortic valve. Features that exploit the geometry of the aortic root may be useful in any delivery approach. Further, it should be understood that any of the features that exploit the aortic root geometry may be applicable to passive commissure-to-commissure alignment in other prosthetic heart valves, such as the tricuspid or pulmonary valve. And even though the mitral valve typically has two leaflets while the aortic valve typically has three leaflets, the passive commissure-to-commissure alignment mechanisms that rely on aortic root or valve geometry may apply with similar or equal force to commissure-to-commissure alignment in mitral valve replacements.

Figure 4A:
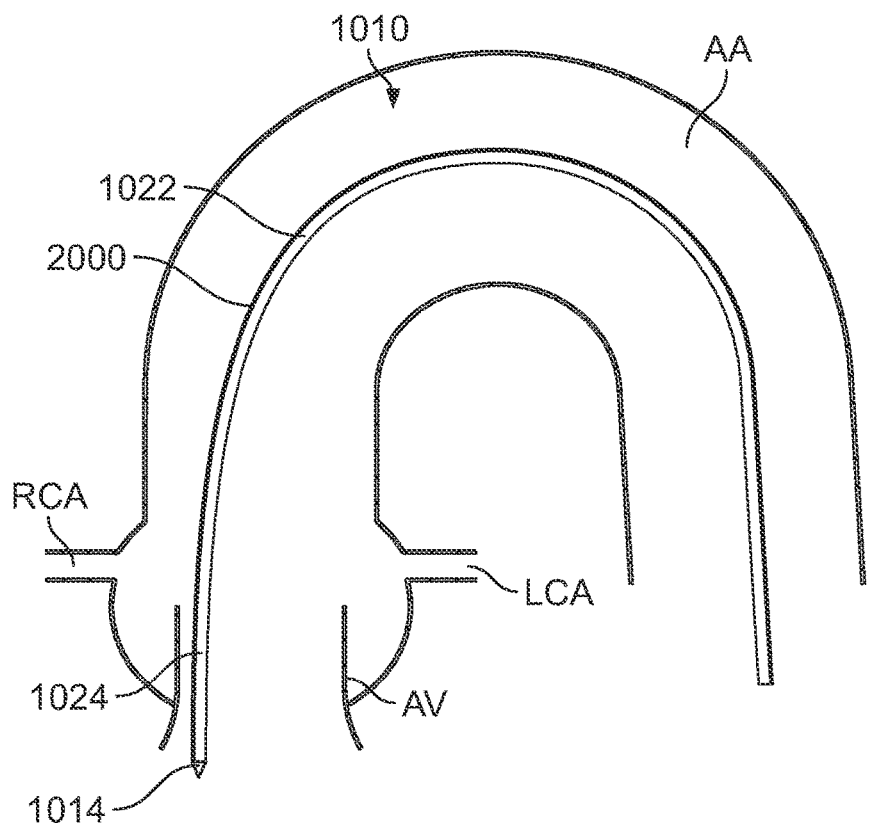
FIG. 4A is a highly schematic side view of a transfemoral delivery device traversing the aortic arch, with a distal end of the delivery device positioned within a native aortic valve.
Figure 4B:
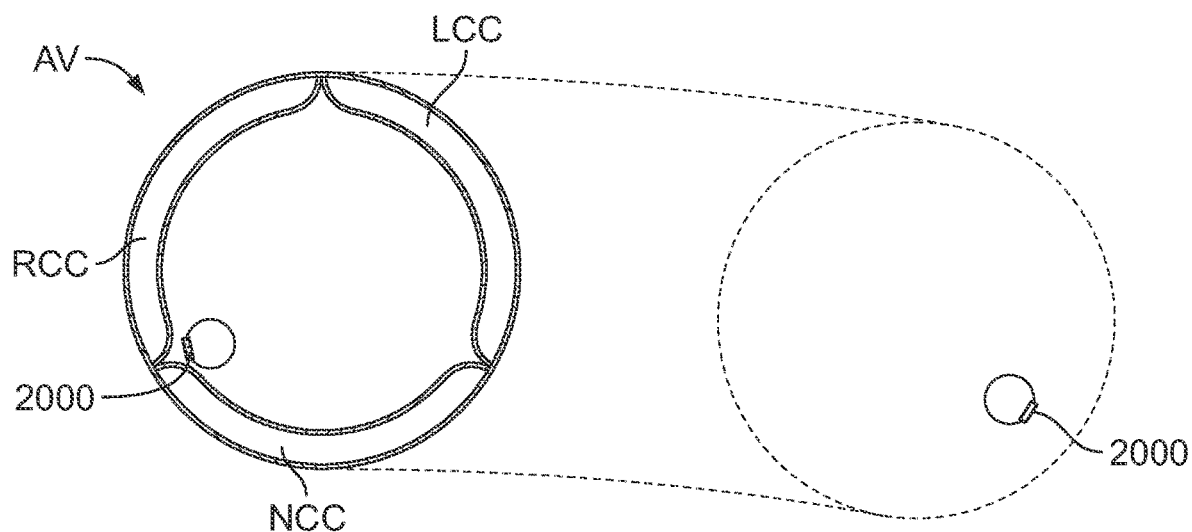
FIG. 4B is a highly schematic cross section of FIG. 4A taken through a plane traversing the aortic arch and the native aortic valve.

FIG. 4A is a highly schematic side view of a delivery device during a transfemoral approach to implant a prosthetic aortic valve, with the delivery device traversing the aortic arch AA and a distal end of the delivery device positioned within or adjacent the native aortic valve AV. The delivery device may be similar or identical to delivery device 1010, with certain additions. However, it should be understood that the concepts described may be used in connection with delivery devices other than delivery device 1010, and the use of the same part numbers for the delivery device in FIGS. 4A-B is purely for convenience. Due to the shape of the aortic arch AA, and due to the stiffness of a given delivery system (such as delivery device 1010), the distal end of the delivery device tends to sit at the outer curvature of the aortic arch AA. The native aortic valve AV typically includes three leaflets, including the left coronary cusp LCC, the right coronary cusp RCC, and the non-coronary cusp NCC, with the left coronary artery LCA and right coronary artery RCA extending from the aorta at a location just downstream the native aortic valve AV. The relative positions of these leaflets are illustrated in FIG. 4B, which is a cross-section taken through a plane that traverses the native aortic valve AV and the descending aortic arch AA. The native commissures are also illustrated in FIG. 4B, at the junction of adjacent ones of the leaflets. Due to the geometry of the aortic arch AA and the stiffness of the delivery device 1010, as noted above, during transfemoral delivery the distal sheath 1024 and distal tip 1014 of the delivery device 1010 tends to follow the outer curvature of the aortic arch AA. The commissure between the right coronary cusp RCC and the non-coronary cusp NCC tends to correspond to this outer curvature location. Thus, as shown in FIG. 4B, the distal end of the delivery device will tend to generally be positioned near this commissure during a transfemoral delivery procedure. It should be understood that the leaflets of the native valve annulus AV is illustrated in the open condition (during ventricular systole) in FIGS. 4A-B.

The delivery device 1010 illustrated in FIGS. 4A-B include an additional feature that may result in a predictable bend orientation (for example by preferentially bending in one direction) when the delivery device is in the position shown in FIGS. 4A-B. This additional feature may help ensure that the distal sheath 1024 housing the prosthetic heart valve (such as prosthetic heart valve 200 or any other expandable prosthetic heart valve) will have a predictable rotational orientation with respect to the native valve commissures. In the illustrated example, delivery device 1010 includes a spine 2000 running along a length thereof. In particular, delivery device 1010 may include a spine 2000 that has a stiffness that is greater than the stiffness of the outer shaft 1022. The spine 2000 may be positioned on the outer diameter of the outer shaft 1022, or otherwise may be embedded within the wall forming the outer shaft 1022. In either case, the spine 2000 may also extend along the distal sheath 1024, including the entire distal sheath or just a portion thereof. The spine 2000 preferably extends at least along the portion of the outer shaft 1022 that will be situated within the aortic arch AA during deployment of the prosthetic heart valve. However, referring to FIG. 4A, the spine 2000 may extend any additional distance proximally toward the handle 1020, including the entire length of the outer shaft 1022.

In one example, the spine 2000 may formed of a metal, metal alloy, or polymer (or combinations thereof) that is stiffer than the material forming the remainder of the outer shaft 1022. The spine 2000 may have a lobster-tail configuration, for example in which the spine 2000 is formed of individual plates or plate-like members in which the leading end of one plate overlaps (or is overlapped by) the trailing end of the adjacent plate. These plates forming spine 2000 may be rectangular in cross-section, or may be generally rectangular in cross-section with a slight curvature that generally follows the circumferential contour of the outer shaft 1022. However, other shapes of these plates may be suitable for use in spine 2000. It should be understood that the overlapping nature of these plates may result in the spine 2000 more easily bending in one desired direction than the opposite direction, as interference between the adjacent plates will be greater in one bend direction compared to the opposite bend direction. In other words, the spine 2000 may preferentially bend so that it is located on the outer radius of the bend. As an alternative or in addition, the spine 2000 may be formed of a shape-memory material (whether in the form of overlapping plates, or in the form of a single continuous wire or other similar member). If formed of shape-memory material, such as a nickel titanium alloy like nitinol, the spine 2000 may be heat-set (or otherwise set) so that the spine 2000 is biased toward bending in one direction compared to other directions. If spine 2000 is in the form of a single continuous member, it may have a rectangular or circular, or oval cross-section, although other shapes may be suitable. The shape-setting may be performed so that the spine 2000 begins to transition (or attempt to transition) to its shape-set contour upon exposure to temperatures found in the body. With this configuration, the spine 2000 may be relatively straight prior to insertion into the body, but after insertion into the body, as the ambient body temperature causes the temperature of spine 2000 to increase, the spine 2000 may begin to transition (or attempt to transition) to its set curvature or set contouring.

In either of these embodiments, it is already known that the outer shaft 1022 (and/or the distal sheath 1024) will tend to be positioned adjacent the native commissure between the right coronary cusp RCC and the non-coronary cusp NCC. By providing the delivery device 1010 with spine 2000 that imparts a preferential bend contour, the delivery device 1010 will tend to have a known rotational orientation when in position for deployment of the prosthetic heart valve. In other words, because the spine 2000 is configured to preferentially bend along the outer curvature of the aortic arch AA, when the delivery device 1010 is in the position shown in FIGS. 4A-B, the spine 2000 will be in or adjacent the native commissure between the right coronary cusp RCC and non-coronary cusp NCC, with the spine 2000 confronting the commissure. Thus, both the spatial position and rotational orientation of the outer shaft 1022 (and/or delivery sheath 1024) will be known with respect to the native aortic valve AV. With this knowledge, the prosthetic heart valve 200 (or any other expandable prosthetic heart valve) may be loaded into the compartment 1023 of the delivery sheath 1024 with one of the prosthetic leaflet commissures rotationally aligned with the position of the spine 2000. Thus, after achieving the position illustrated in FIGS. 4A-B, the distal sheath 1024 may be withdrawn to allow the prosthetic heart valve 200 to expand into the native aortic valve AV. This relative positioning will result in the prosthetic commissure originally rotationally aligned with the spine 2000 being rotationally aligned with the native commissure between the right coronary cusp RCC and then non-coronary cusp NCC after deployment. Further, it should be understood that if one of the prosthetic commissures is rotationally aligned with one of the native commissures, the remaining prosthetic commissures will be generally in rotational alignment with the remaining native commissures.

Although any suitable method may be used to help ensure that one of the commissures of the prosthetic heart valve 200 is aligned with the spine 2000 during loading of the prosthetic heart valve into the delivery device 1010, one particular method may rely on the positions of the retainers 1025 of the delivery device. As described above, the prosthetic heart valve 200 may be held in a desired axial and rotational position within the compartment 1023 due to the retaining elements 218 of the prosthetic heart valve being received in corresponding retainers 1025. Referring back to FIG. 1, each of the three retainers 218 is axially aligned with one of the prosthetic commissures, which are positioned at the commissure attachment features 216 of the stent 202. Thus, if the spine 2000 is rotationally aligned with one of the retainers 1025, the prosthetic heart valve 200 will have one of the prosthetic commissures aligned with the spine 2000 during loading due to the relative positioning of the retainers 1025, the retaining elements 218, and the commissure attachment features 216.

Figure 5A:
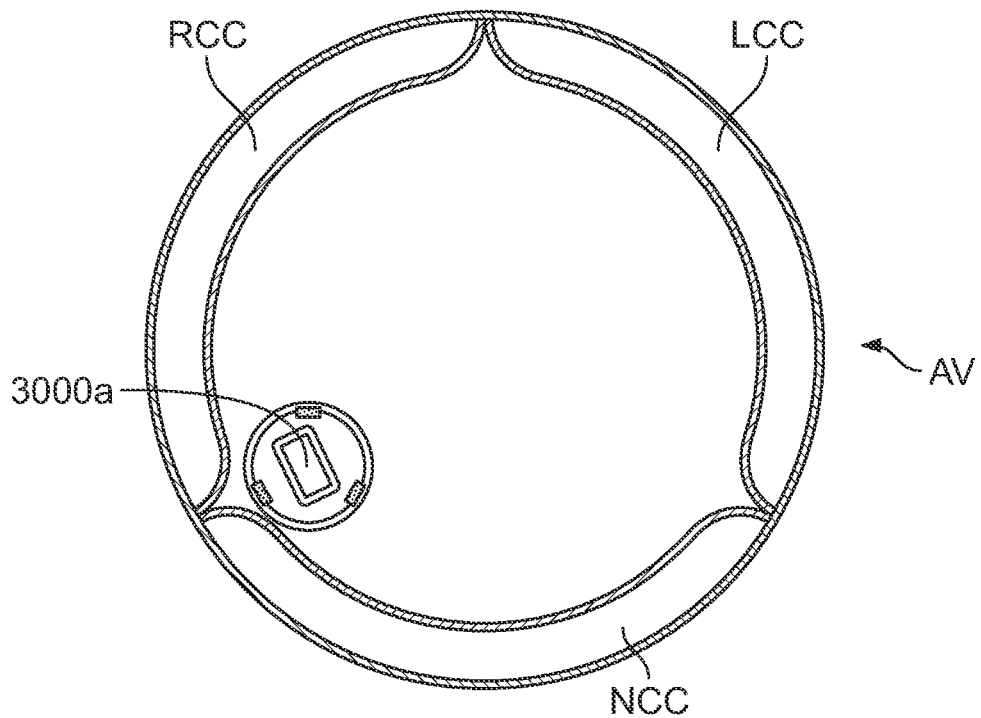
FIGS. 5A-B are cross-sections of a delivery device positioned within a native aortic valve, the delivery device including rectangular and circular interior spines, respectively.
Figure 5B:
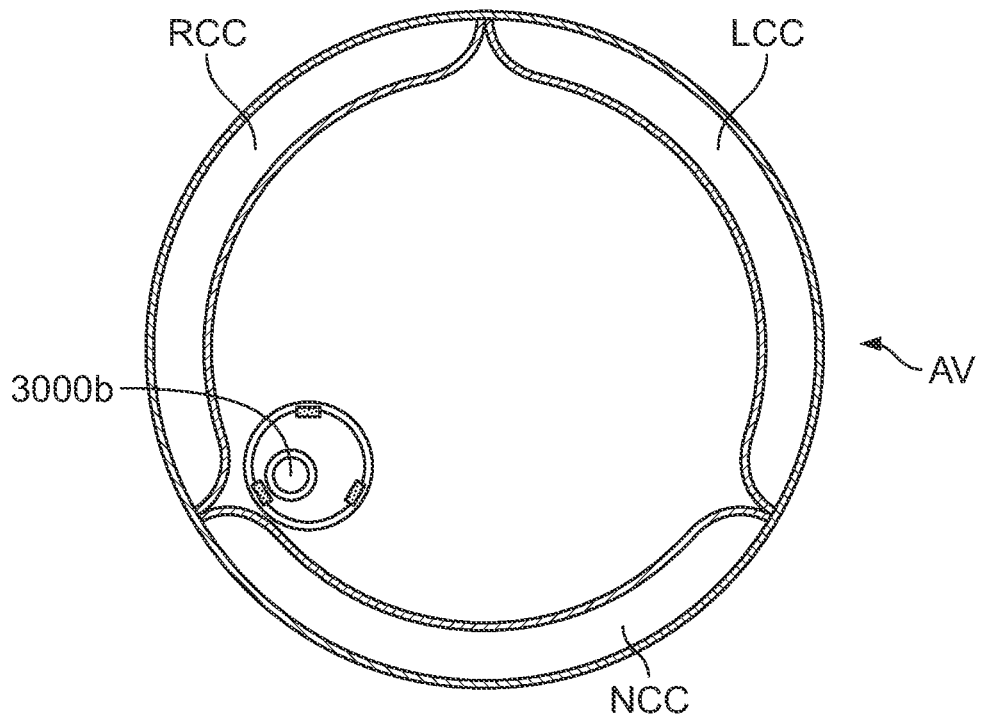

While FIGS. 4A-B focus on a spine 2000 positioned on or adjacent an outer diameter of the outer shaft 1022 and/or distal sheath 1024 of the delivery device 1010, FIGS. 5A-B illustrate a related concept where a spine is positioned on an interior of the delivery device. In particular, FIG. 5A illustrate a spine 3000a having a rectangular cross-section, whereas spine 3000b has a generally circular cross-section. Spines 3000a-b may be formed of a relatively rigid material that extends a length along the delivery device 1010, similar to that described in connection with spine 2000, but positioned on the interior of the outer shaft 1022. Spines 3000a-b generally serve the same overall purpose as spine 2000 to induce preferential bending of the outer shaft 1022 around the aortic arch AA. Spines 3000a-b may be formed of a metal, metal alloy, polymer, or combinations thereof that are preferably more rigid and/or stiff than the outer shaft 1022, and may extend a length relative to the inner shaft 1022 similar to that described in connection with spine 2000. The preferential bending may be induced by shape-memory setting of the spines 3000a-b and/or by the geometry and position of the spines 3000a-b relative to the remainder of the outer shaft 1022. For example, the spines 3000a-b may be shape-set in substantially the same manner described above in connection with spine 2000. Whether or not the spines 3000a-b are shape-set, they may include geometries and positions that induce a particular bend. For example, spine 3000a may have a rectangular cross section transverse its length. This rectangular shape will cause spine 3000a to preferentially bend so that the longer sides of the rectangular are positioned on the inner and outer tracks of the bend, while the shorter sides are positioned on either side of the bend. The spine 3000a may be positioned generally centered along the center longitudinal axis of the outer shaft 1022. FIG. 5A also illustrates the rotational positions of the prosthetic commissures (or retaining elements 218, retainers 1025, or commissure attachment features 216) when the prosthetic heart valve 200 is within the delivery device 1010. As can be seen in FIG. 5A, one of the prosthetic commissures is positioned generally centered along one of the longer sides of the rectangular cross-section of the spine 3000a. With this relative positioning, one of the longer sides of the spine 3000a will tend to confront the native commissure, as shown in FIG. 5A, and thus one of the prosthetic commissures will tend to rotationally align with the native commissure between the right coronary cusp RCC and the non-coronary cusp NCC. Thus, when loading the prosthetic heart valve 200 (or any other prosthetic heart valve) into the delivery sheath 1024, the prosthetic heart valve is preferably loaded so that one of the prosthetic commissures is in rotational alignment with the longer side of the spine 3000a that will tend to confront the native commissure. As with the embodiments above, this can be achieved, for example, by aligning the retainers 1025 in the desired rotational orientation relative to the spine 3000a.

Now referring to FIG. 5B, spine 3000b may function generally similar to spine 3000a, with two main differences. First, spine 3000b may have a generally circular cross-section. However, if spine 3000b does not include shape-setting, it would may induce any preferential bending if the center longitudinal axis of the spine 3000b was coincident with the central longitudinal axis of the outer shaft 1022. Instead, the central longitudinal axis of the spine 3000b may be offset from the central longitudinal axis of the outer shaft 1022. In particular, by offsetting these central longitudinal axes, the outer shaft 1022 will tend to bend so that the spine 3000b is positioned closer to the outer radius of the bend than the inner radius of the bend. Thus, the prosthetic heart valve should be loaded into the distal sheath 1024 so that one of the prosthetic commissures is generally rotationally aligned with the point along the spine 3000b that is closest in distance to the outer shaft 1022. As with the embodiments above, this can be achieved, for example, by aligning the retainers 1025 in the desired rotational orientation relative to the spine 3000b. It should be understood that the delivery of the prosthetic heart valve 200 (whether using spine 3000a or 3000b) may be otherwise substantially the same as that described in connection with FIGS. 4A-B. The embodiments described in connection with FIGS. 4A-5B may be best suited for transfemoral aortic valve replacement, at least in part because these embodiments rely on the curvature of the aortic arch AA to passively achieve the desired commissures-to-commissure alignment. Further, it should be understood that any of the spines described above maybe substantially or completely solid members.

While the embodiments described in connection with FIGS. 4A-5B mainly leverage the shape and contours of the aortic arch AA, the embodiments described below in connection with FIGS. 6A-8B may rely on the geometry of the aortic root (including the native aortic valve AV) to achieve the desired commissure-to-commissure alignment, although the shape of the aortic arch AA may also be implicated in these embodiments.

Figure 6A:
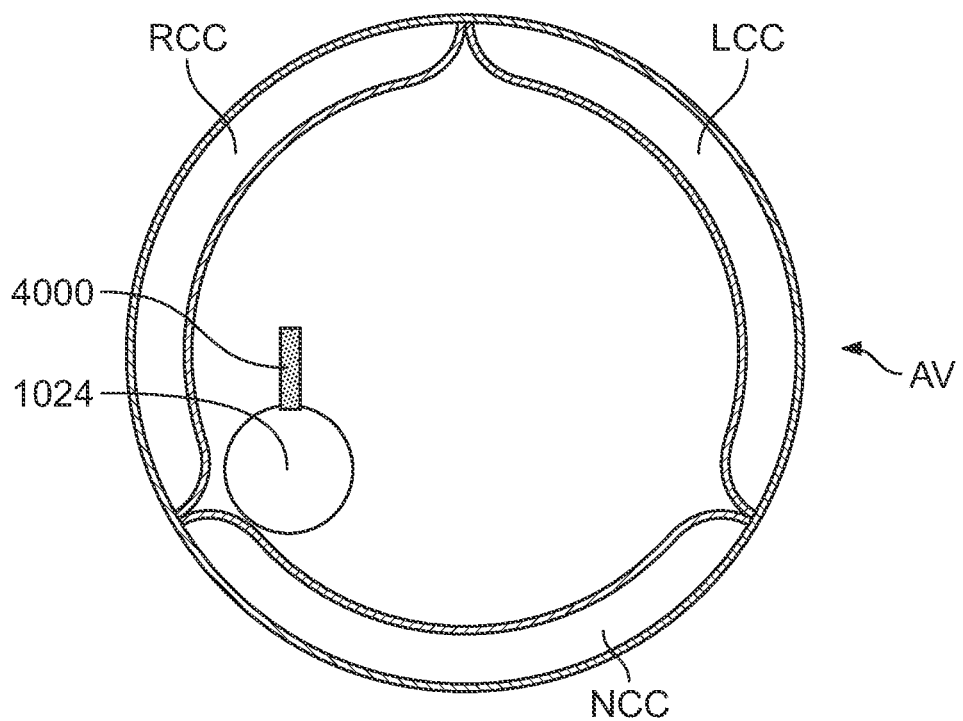
FIGS. 6A-B are cross-sections of a delivery device positioned within the native aortic valve during ventricular systole and ventricular diastole, respectively.
Figure 6B:
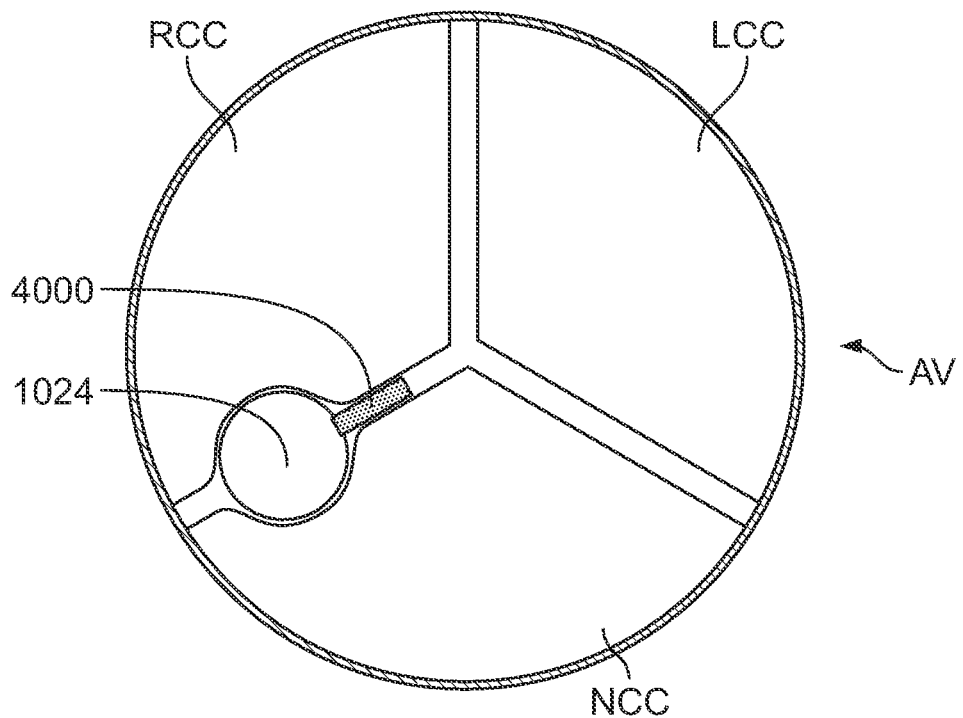

The embodiments of FIGS. 6A-7B include a delivery device 1010 that may be similar or identical to that described in connection with FIG. 3, with certain differences. FIG. 6A illustrates a cross-section of the distal sheath 1024 of the delivery device 1010 positioned within the native aortic valve AV while the valve leaflets are open (e.g. during ventricular systole), while FIG. 6B provides the same illustration but after the leaflets are closed (e.g. during ventricular diastole). As shown in FIGS. 6A-B, the distal sheath 1024 may include a fin-like protrusion 4000 extending radially outward therefrom. Protrusion 4000 may extend a length along the distal sheath 1024, for example at least about 20%, at least about 40%, at least about 60%, at least about 80%, or the entire length of the distal sheath 1024. The protrusion 4000 may extend a length radially outwardly from the outer surface of the distal sheath 1024 that is about the same diameter of the distal sheath 1024, although in other embodiments length may be greater or smaller than the diameter of the distal sheath 1024. Preferably, the protrusion 4000 is formed of a material similar to that of the distal sheath 1024, although other materials may be suitable. In some embodiments, the protrusion 4000 may be integral with the distal sheath 1024, and in other embodiments the protrusion 4000 may be formed separately and coupled to the distal sheath 1024. In some embodiments, the protrusion 4000 may be formed as an inflatable member, similar to valvuloplasty balloons, so that the protrusion 4000 can be inflated via saline or other solution when in the desired position, reducing the overall profile of the distal sheath 1024 during delivery and prior to the use of the protrusion 4000. The protrusion 4000 preferably does not extend proximal to the distal sheath 1024 to the outer shaft 1022, although in some embodiments that extension may be suitable.

As is described in greater detail below in connection with FIGS. 8A-B, the delivery device 1010 shown in connection with FIGS. 6A-7B may include features that allow the distal sheath 1024 to rotated with respect to the outer shaft 1022, for example where the outer shaft 1022 transitions to the distal sheath 1024. Referring back to FIG. 6A, when the distal sheath 1024 is positioned within the native aortic valve AV, the protrusion 4000 is also positioned within the native aortic valve AV. As with the earlier embodiments described in connection with FIGS. 4A-5B, if the delivery route is transfemoral and through the aortic arch AA, the distal sheath 1024 will tend to be positioned at or near the commissure between the right coronary cusp RCC and the non-coronary cusp NCC. When in this position, the protrusion 4000 extends radially inwardly, generally pointing away from the native commissure between the right coronary cusp RCC and the non-coronary cusp NCC, although the exact direction may depend on various factors during the delivery. As the heart continues to beat, the leaflets of the native aortic valve AV will be forced closed during ventricular diastole, as shown in FIG. 6B. As the leaflets coapt, the right coronary cusp RCC and the non-coronary cusp NC will attempt to close over the distal sheath 1024 and the protrusion 4000. Because the distal sheath 1024 is rotatable relative to the outer shaft 1022, the force of the leaflets closing over the protrusion 4000 will tend to rotate the distal sheath 1024 so that the protrusion 4000 extends along the line of coaptation between the right coronary cusp RCC and the non-coronary cusp NCC. This position is illustrated in FIG. 6B, with the radial end of the protrusion 4000 pointing toward the longitudinal center of the native aortic valve AV.

Similar to earlier embodiments, with the configuration described in connection with FIGS. 6A-B, the spatial position of the distal sheath 1024 will generally be known (i.e. in or near the native commissure between the right coronary cusp RCC and the non-coronary cusp NCC) at least in part due to the tendency of the delivery device to hug the outer radius of the aortic arch AA. Further, the rotational position of the distal sheath 1024 will be known due to the forced repositioning of the protrusion 4000 to orient along the line of coaptation toward the valve center. Thus, the prosthetic heart valve 200 (or any other suitable prosthetic heart valve) can be loaded into the distal sheath 1024 with the prosthetic commissures in a particular desired rotational orientation. For example one of the prosthetic commissures may be positioned diametrically opposed to the point where the protrusion 4000 contacts (or extends from) the distal sheath 1024. With this configuration, when the distal sheath 1024 is in the position and orientation shown in FIG. 6B, one of the prosthetic commissures will rotationally align with the native commissure between the right coronary cusp RCC and the non-coronary cusp NCC. Thus, as the distal sheath 1024 is withdrawn to allow the prosthetic heart valve 200 to self-expand (or to expand via a balloon or similar mechanism), the native and prosthetic commissures will be in rotational alignment. As with other embodiments, the prosthetic heart valve 200 may be loaded into the distal sheath 1024 with the desired orientation in any suitable manner, including by positioning the protrusion 4000 diametrically opposed one of the retainers 1025. The process of implanting the prosthetic heart valve 200 may be otherwise similar or the same as described for embodiments above.

Figure 7A:
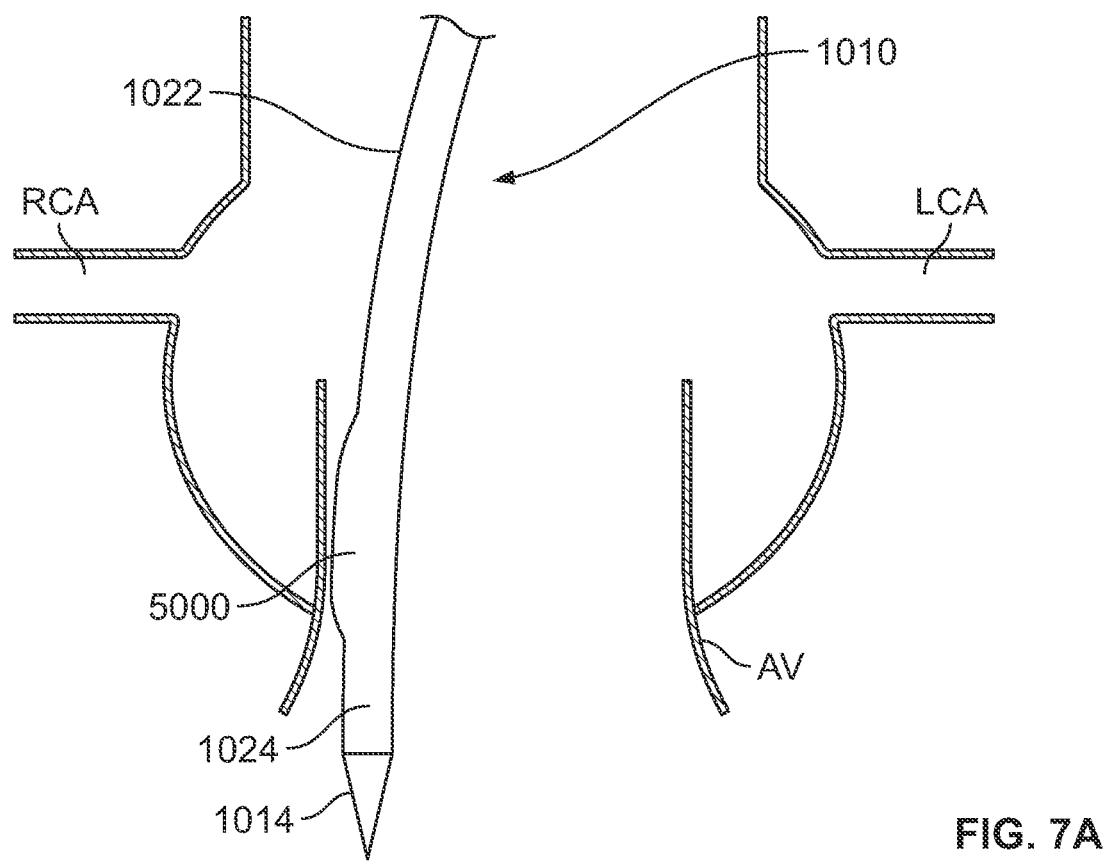
FIG. 7A is a highly schematic side view of a transfemoral delivery device with a distal end of the delivery device that includes a protrusion positioned within a native aortic valve.
Figure 7B:
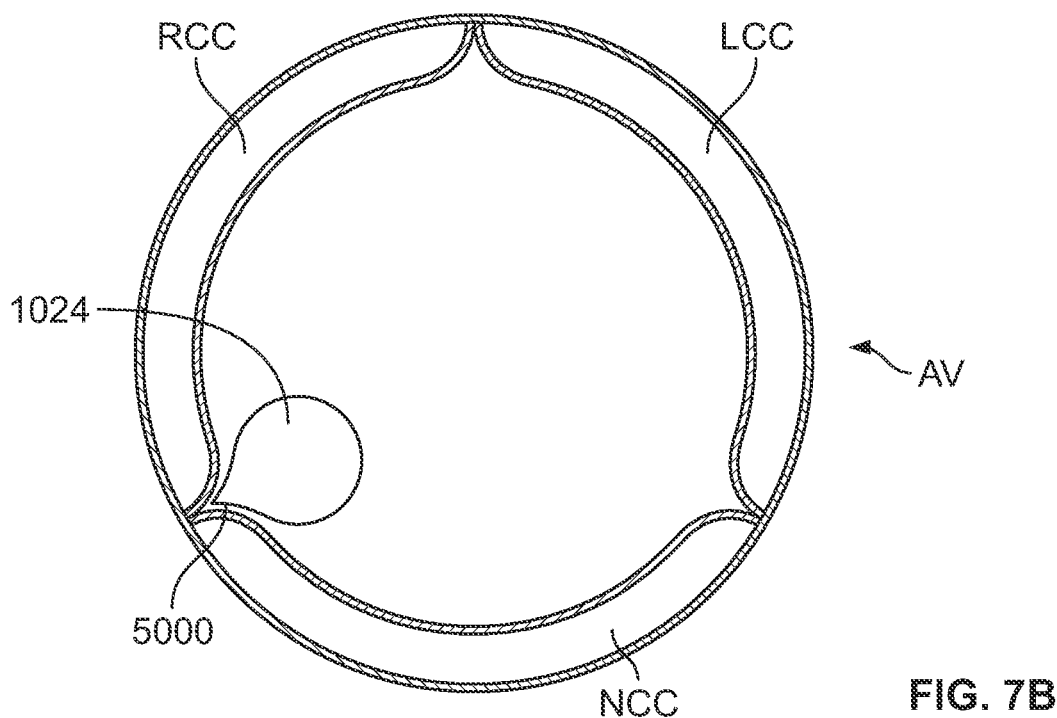
FIG. 7B is a highly schematic cross section of FIG. 7A taken through a plane traversing the native aortic valve.
Figure 8A:
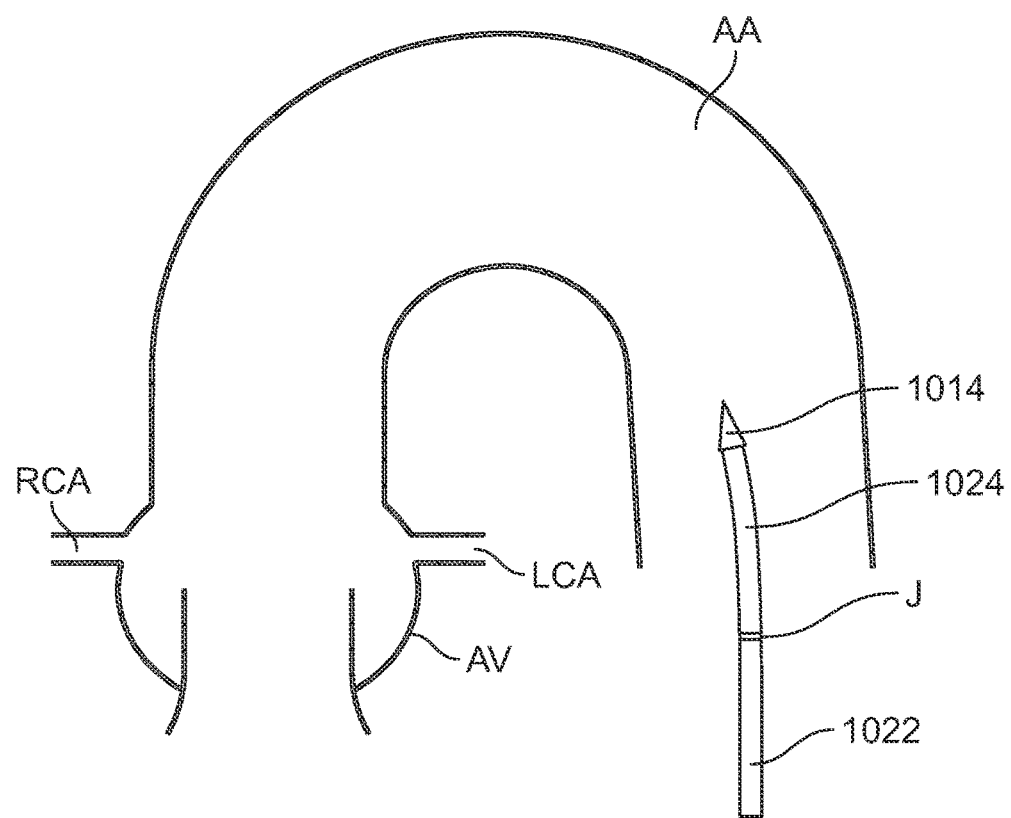
FIG. 8A is a highly schematic side view of a transfemoral delivery device traversing the aortic arch, with a distal end of the delivery device being rotatable relative to another portion of the delivery device.
Figure 8B:
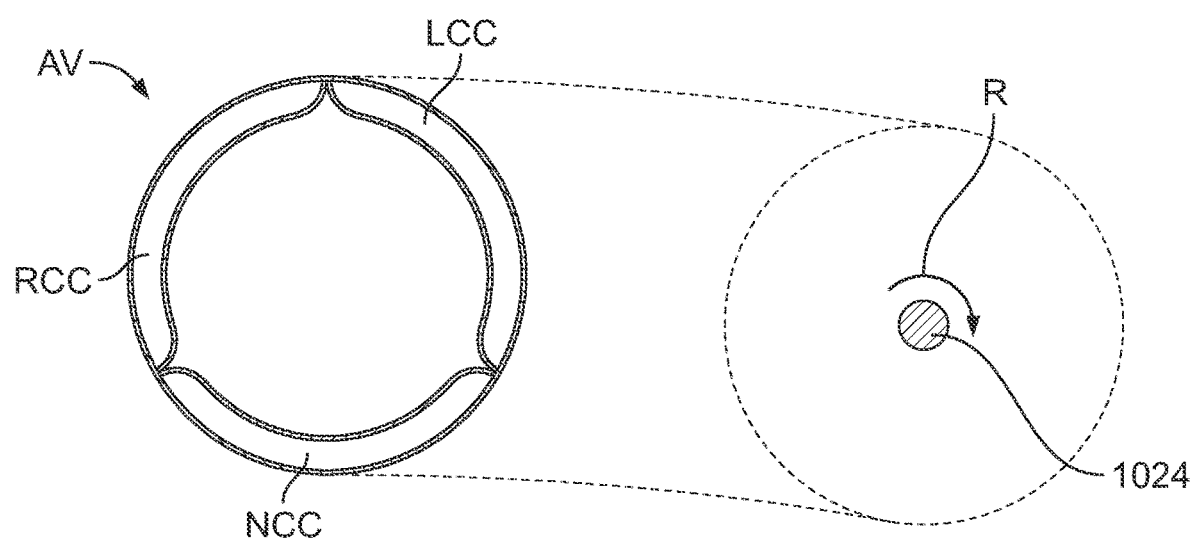
FIG. 8B is a highly schematic cross section of FIG. 8A taken through a plane traversing the aortic arch, illustrating the rotation of the delivery device.

FIGS. 7A-7B illustrate a delivery device 1010 that is generally similar to that described in connection with FIGS. 6A-6B, with certain differences. The main difference is that, while the embodiment shown in connection with FIGS. 6A-B includes a relatively long (in radial extension) and thin protrusion 4000, the embodiment of FIGS. 7A-B include a distal sheath 1024 that has a non-symmetric cross-sectional shape with a protrusion 5000 that has a shape complementary to the native commissure. Referring to FIG. 7A, the protrusion 5000 on the distal sheath 1024 may be positioned only on the distal sheath 1024 and may not extend proximally to the outer shaft 1022 beyond the point where the outer shaft 1022 transitions to the distal sheath 1024. As is described in greater detail below, the distal sheath 1024 may be rotatable relative to the outer shaft 1022, similar to the embodiment described in connection with FIGS. 6A-B. Preferably, the protrusion 5000 is integrally formed with the distal sheath 1024, and may have the shape of a slight triangular protrusion extending from an otherwise circular cross-section, as shown in FIG. 7B. The protrusion 5000 may be significantly smaller than protrusion 4000 in radial extension, but significant longer than protrusion 4000 in axial extension. For example, the length of the protrusion may be about half, less than half, or less than one fourth the diameter of the distal sheath 1024 (where the diameter of the distal sheath 1024 is exclusive of the protrusion 5000). The shape and size of the protrusion 5000 may be generally complementary to (or a negative of) the shape the native commissure between the right coronary cusp RCC and the non-coronary cusp NCC. As noted above, if a transfemoral delivery route is used, the traversal of the aortic arch AA may generally cause the distal sheath 1024 to be positioned near or adjacent the native commissure, as shown in FIG. 7B. If the protrusion 5000 does not initially nest into the native commissure, the freedom of the distal sheath 1024 to rotate will result in the distal sheath 1024 rotating until the protrusion 5000 fits into the native commissure, like a puzzle piece, as shown in FIG. 7B. Once the protrusion 5000 nests within the native commissure, the puzzle-like fitment will prevent the distal sheath 1024 from additional rotation, effectively locking the rotation position of the distal sheath 1024 relative to the native aortic valve AV during deployment of the prosthetic heart valve 200.

Once the distal sheath 1024 is positioned within the native valve annulus AV and the protrusion 5000 has rotated into fitment with the native commissure, the distal sheath 1024 may be retracted to deploy the prosthetic heart valve 200 while the position and rotational orientation of the prosthetic heart valve are in the desired relation to the native commissures. In particular, the prosthetic heart valve 200 (or any other suitable prosthetic heart valve) is loaded into the distal sheath 1024 with one of the prosthetic commissures in rotational alignment with the protrusion 5000. With this configuration, one of the prosthetic commissures will be in rotational alignment with the native commissure between the right coronary cusp RCC and the non-coronary cusp NCC, while the other two prosthetic commissures will be in rotational alignment with the other two native commissures on completion of deployment. As with the other embodiments described herein, the prosthetic heart valve 200 may be loaded into the distal sheath 1024 with the desired orientation in any desirable fashion, including by positioning the protrusion 5000 in radial alignment with one of the retainers 1025. The remainder of the delivery and deployment of the prosthetic heart valve may be similar or identical to that described in connection with other embodiments above.

The embodiments described in connection with FIGS. 6A-7B rely, in part, on the ability of the distal sheath 1024 to rotate with respect to the outer shaft 1022 while the delivery device 1010 is positioned at or near the native aortic valve AV. Such rotation may be achieved via any suitable mechanism. FIG. 8A illustrates the delivery device 1010 including a joint J between the outer shaft 1022 and the distal sheath 1024. The joint J may take the form of a rotary bearing, such as a thrust bearing, that allows for rotation of the outer sheath 1024 in one rotational direction R or in both rotational directions about the longitudinal axis of the outer shaft 1024, as shown in FIG. 8B. However, it should be understood that other rotational joints J may be suitable other than thrust bearings. In some embodiments, it may be preferable to have friction about the joint J so that, while the distal sheath 1024 can rotate, the rotation is not totally free. For example, referring back to FIG. 6B, the joint J needs to be able to rotate toward the valve center when the leaflets close on the protrusion 4000. However, when the leaflets open again during ventricular systole, it may be preferable for some resistance in the joint J to help maintain the rotational position of the protrusion when the leaflets are not actively pushing the protrusion.

Figure 9A:
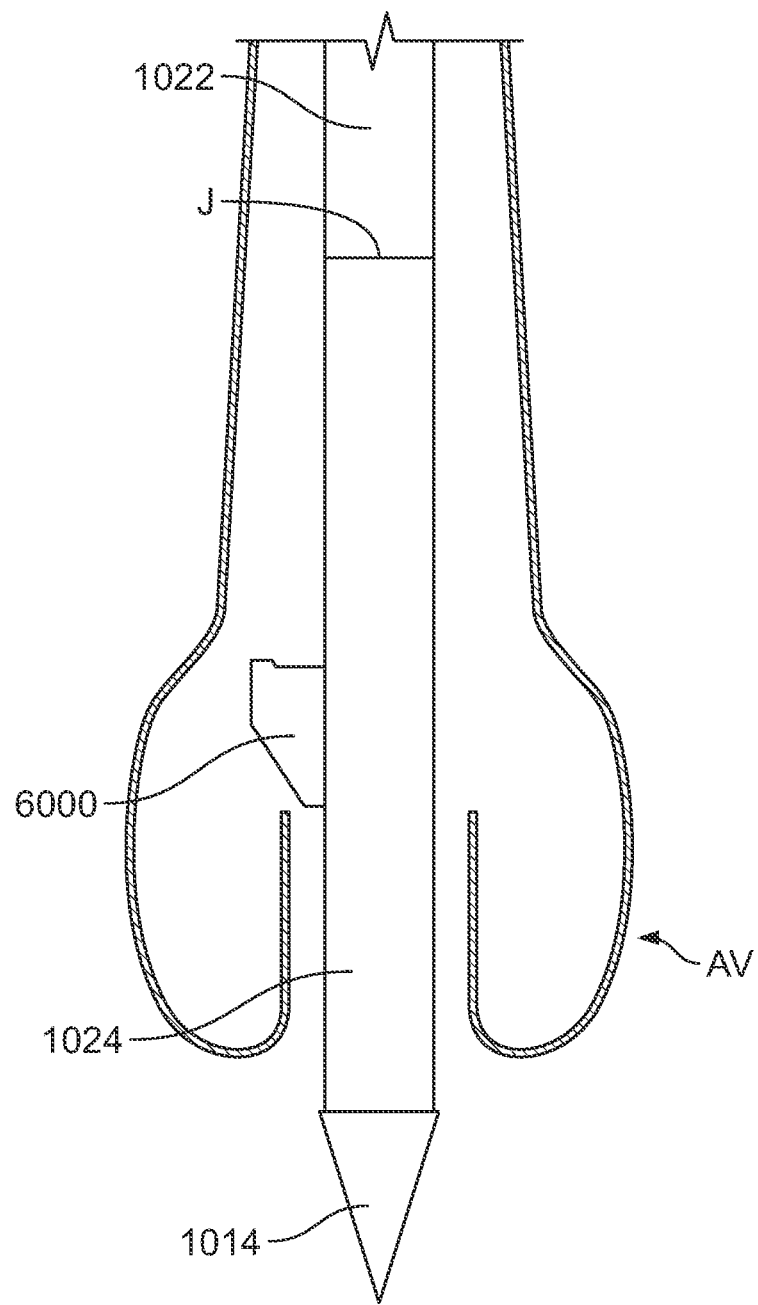
FIG. 9A is a highly schematic side view of a transfemoral delivery device positioned within a stenotic native aortic valve.

FIG. 9A illustrates another embodiment of the delivery device 1010 that may assist in passive commissure-to-commissure alignment, particularly in stenotic native aortic valves AV. FIG. 9A illustrates a delivery device similar to that described in connection with FIGS. 8A-B, including a joint J that allows rotation between the distal sheath 1024 and the outer shaft 1022. The main difference in the embodiment shown in FIG. 9A is that the distal sheath 1024 includes a fin 6000. The fin 6000 may be thin and may protrude radially outward from the distal sheath 1024. The fin 6000 may be shaped so that the distance is ramped in a proximal to distal direction. In other words, the radial distance which the fin 6000 extends from the distal sheath 1024 may increase from the distal end of the fin 6000 towards the proximal end of the fin 6000. In the particular illustrated embodiment, the fin 6000 first ramps outwardly from the outer sheath 6000, and then maintain that distance for a length. This shape may be particularly useful in stabilizing the fin 6000 as fluid (i.e. blood) flows over the fin 6000, as described in greater detail below.

Figure 9B:
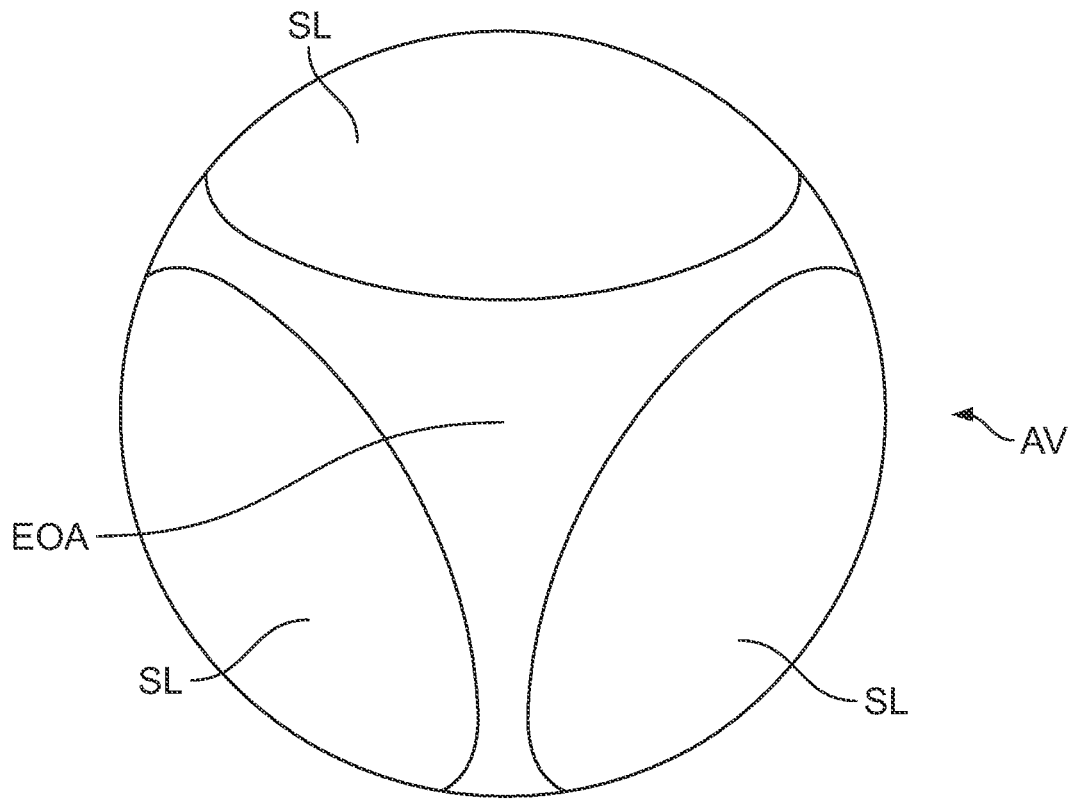
FIG. 9B is a highly schematic cross-section of the stenotic native aortic valve in FIG. 9A in an open condition.

FIG. 9B illustrates a highly schematic cross section of a stenotic aortic valve AV with three stenotic leaflets SL during ventricular systole. The relatively high level of stenosis of the leaflets SL results in a relatively small effective orifice area EOA when the leaflets are open. This difference can be qualitatively seen by comparing the open stenotic leaflets SL of the aortic valve AV of FIG. 9B with the size and shape of the open area of the aortic valve in FIG. 7B. This smaller effective orifice area EOA may result in a higher velocity of blood through the aortic valve during ventricular systole, although it should be understood that the embodiment described in connection with FIGS. 9A-C may be suitable for use in aortic valve AV that have less stenosis than that shown in FIG. 9B.

Figure 9C:
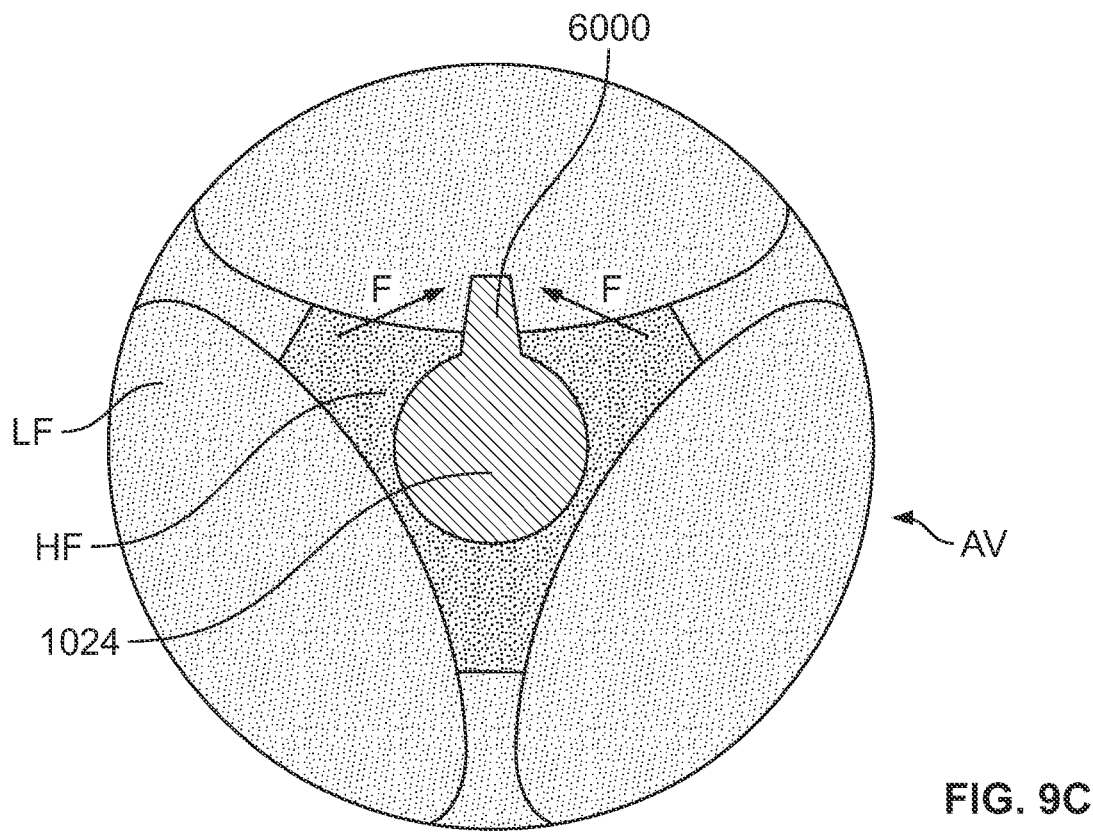
FIG. 9C is a highly schematic cross-section of the stenotic native aortic valve in FIG. 9A in the open

FIG. 9C illustrates the aortic valve AV of FIG. 9B with the distal sheath 1024 positioned substantially aligned with the center of the aortic valve AV, and with the fin 6000 positioned slightly downstream of the stenotic leaflets SL. When the aortic valve AV is open, the area of high velocity blood flow HF is restricted to the center area, with the remainder area having low velocity blood flow LF, as indicated in FIG. 9C. As the blood flows through the aortic valve AV while the fin 6000 is positioned just downstream the stenotic leaflets SL, the shape of the particular fin 6000 illustrated in FIGS. 9A and 9C will result in the fin 6000 orienting to a low flow position. For example, as shown in FIG. 9C, forces F from the high flow area HF will tend to push the fin 6000 away from the high flow HF zones until the fin 6000 stabilizes in a low flow area LF. In this particular embodiment, the fin 6000 is preferably positioned a spaced distance from the distal tip 1014 so that, when the distal sheath 1024 is within the aortic valve AV, the closing of the stenotic leaflets SL does not contact the fin 6000 and does not cause the distal sheath 1024 to rotate. When loading the prosthetic heart valve 200 (or any other suitable heart valve) within the distal sheath 1024, one of the prosthetic commissures may be positioned diametrically opposed to the location of the fin 6000. Thus, when the fin 6000 is in the position shown in FIG. 9C, one of the prosthetic commissures is rotationally aligned with the bottom of the aortic valve AV in the view of FIG. 9C, which is where one of the native commissures is positioned. Upon deploying the prosthetic heart valve 200, then, the prosthetic commissures will rotationally align with corresponding native commissures.

Although one shape of fin 6000 is illustrated, other shapes may be used to position the fin into a high flow area HF, a low flow area LF, or to cause the fin to rotate until it contacts one of the leaflets. For example, if the fin has a wedge, funnel, or shovel shape, the fin would tend to align away from the high flow HF areas and to settle in a low flow LF area, similar to the view of FIG. 9C. An umbrella or airfoil shape, on the other hand, would tend to cause the fin to move toward and settle in a high flow HF area. If the fin has one of these shapes to align with a high flow HF area, one of the prosthetic commissures should be aligned with the fin (instead of diametrically opposed from the fin) when the valve is loaded into the distal sheath 1024. In the above embodiments, the fins are preferably positioned just downstream and clear of the leaflets so that the leaflet closing does not interfere with the leaflets. However, in other embodiments, the fins may be positioned so that the leaflets can contact the fin to further assist with the alignment. In other embodiments, the fin can be angled or have a corkscrew shape so that, as blood flows over the fin, the fin initiates rotation in the delivery system capsule/compartment. In this embodiment, the fin is preferably in an axial position so that the delivery system capsule will rotate until it makes contact with one of the native leaflets forcing the delivery system into the native commissure.

Figure 10A:
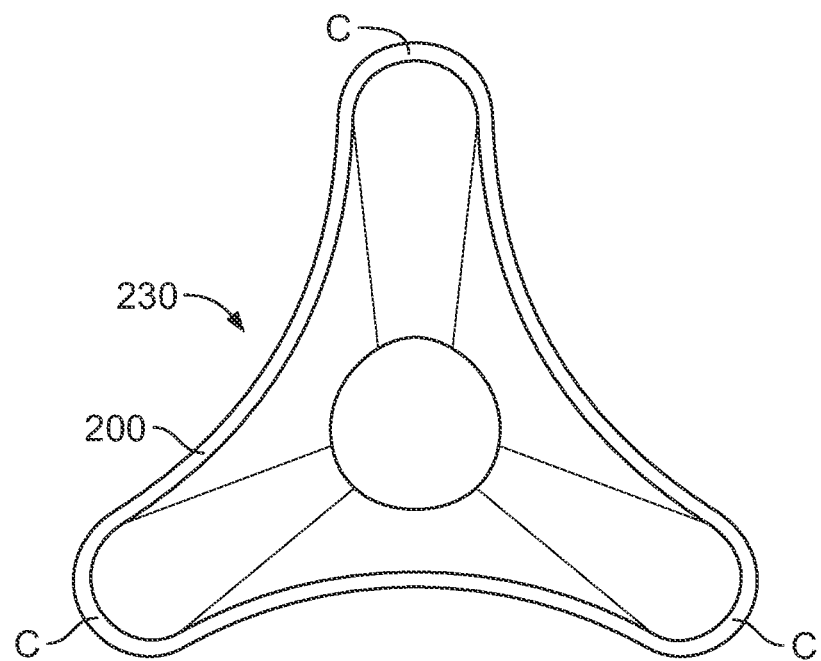
FIG. 10A is a highly schematic view of the inflow end of a prosthetic heart valve mid-deployment from a delivery device.
Figure 10B:
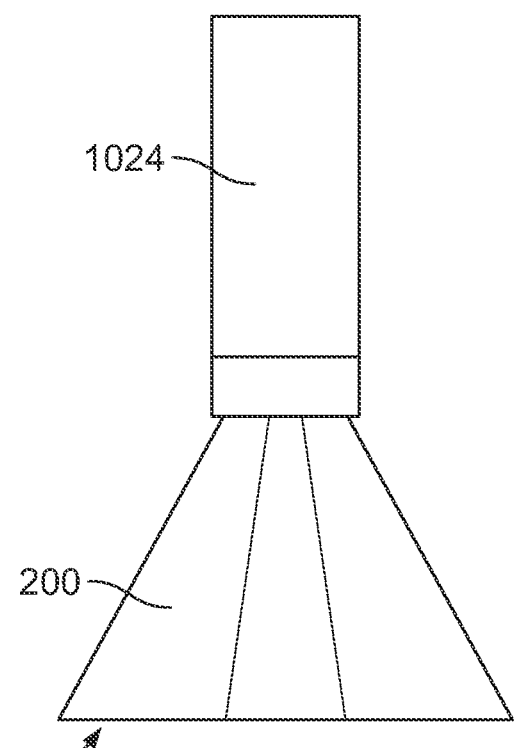
FIG. 10B is a side view of the prosthetic heart valve of FIG. 10A mid-deployment.

While many of the embodiments above focus on features related to the delivery device to assist in commissure-to-commissure alignment, in other embodiments, the prosthetic heart valve 200 may include features that assist in commissure-to-commissure alignment. For example, prosthetic heart valve 200 may be provided with a particular shape during deployment that may be useful in providing the desired commissure-to-commissure alignment. FIGS. 10A-B illustrate prosthetic heart valve 200 mid-deployment from the distal sheath 1024, with the inflow end 230 of the prosthetic heart valve 200 transitioning to the expanded condition, and the outflow end 232 still maintained within the distal sheath in a collapsed condition, for example via connection of retaining elements 218 to retainers 1025. As can be best seen in FIG. 10A, prosthetic heart valve 200 is configured to take a particular shape during deployment. In FIG. 10A, the shape is generally triangular, with the points of the triangle shape being aligned with the prosthetic commissures C of the valve (and with the commissure attachment features 216 and/or retaining elements 218). The profile of the prosthetic heart valve 200 may include curved or concave contours between adjacent commissures C while the prosthetic heart valve 200 is partially deployed. Preferably, if the prosthetic heart valve 200 includes the above-described shape (or any similar shape) mid-deployment, the distal sheath 1024 is rotatable relative to the outer shaft 1022, similar to as described above, for example in connection with FIGS. 8A-B. With this configuration, as the prosthetic heart valve 200 is deployed from the distal sheath 1024, the profile of the inflow end 230 of the prosthetic heart valve 200 has a shape that generally corresponds to the native aortic valve AV while the inflow end 230 is positioned at least partially within the native aortic valve AV. As the native leaflets close during ventricular diastole, the leaflets will tend to try to push against the contoured surfaces of the prosthetic heart valve 200 between adjacent commissures C. Because the distal sheath 1024, and thus the prosthetic heart valve 200, is capable of rotating relative to the outer shaft 1022, when the native leaflets push against the inflow end 230 of the prosthetic heart valve 200, they will tend to force the prosthetic heart valve 200 into alignment with the native aortic valve geometry. In other words, the commissures C of the prosthetic heat valve 200 will tend to rotationally align with the native commissures due to the forces applied on the prosthetic heart valve 200 by the native leaflets closing.

It should be understood that, while the configuration of the partial deployment shape of the prosthetic heart valve 200 described in connection with FIGS. 10A-B may be useful for passive commissure-to-commissure alignment, it may also be useful for active commissure-to-commissure alignment. For example, if the delivery device 1010 is provided with a mechanism to actively rotate the distal sheath 1024, the partially deployed valve can be actively rotated until it is in the desired rotational orientation (which may be confirmed, for example, under fluoroscopy), and then rotation of the distal sheath 1024 may then be locked so that the prosthetic heart valve 200 is unable to rotate out of the desired orientation during the remainder of deployment.

While the partially deployed shape shown and described in connection with FIGS. 10A-B is generally triangular, other shapes may be suitable. For example, an egg shape (in the view of FIG. 10A) may also produce similar results, with the narrow end of the "egg" shape tending to rotated toward a commissure. Thus, in that embodiment, one of the prosthetic commissures would be positioned in radial alignment with the narrow point of the egg shape. However, other partial deployment shapes may also be suitable as long as those shapes tend to self-rotate (or allow for active rotation) into a predictable position relative to the native commissures.

The above-described shapes of the prosthetic heart valve 200 during partial deployment may be achievably by any suitable means. In one example, the prosthetic heart valve 200 may be tethered to the delivery device 1010, with the tethers applying force to constrain the prosthetic heart valve into the desired partial deployment shape. For example, tethers such as sutures may be attached to the stent of the prosthetic heart valve near the middle of the concave curvature sections of FIG. 10A and extend up through the delivery device 1010 so that tension on the tethers restricts the expansion of the inwardly contoured sections. The tethers may be cut or may have a reversible looping system in order to release the tethers from the prosthetic heart valve 200 after implantation is complete. In another embodiment, a plurality of arms may extend distally from the distal sheath 1024 (e.g. from the outer surface of the distal sheath 1024), with the arms configured to press inwardly on the prosthetic heart valve 200 during deployment. For example, in connection with the embodiment of FIGS. 10A-B, three arms may extend distally from the distal sheath 1024 to contact the outer surface of the prosthetic heart valve 200 during deployment to block the contact portions from fully expanding while the contact is maintained. With this configuration, the arms may rotate in sync with the distal sheath 1024 as deployment progresses and the prosthetic heart valve 200 rotates into commissural alignment with the native heart valve. It should be understood that as deployment continues and the distal sheath 1024 is withdrawn further, the arms move out of contact with the prosthetic valve and allow the prosthetic valve 200 to fully expand. If arms are included to force the desired mid-deployment shape, those arms may be retractable into the delivery device so as to not interfere with the anatomy during delivery or withdrawal of the delivery device. In another embodiment, the delivery device 1010 may include a secondary distal sheath or sleeve positioned distal to distal sheath 1024. The secondary distal sheath may include recesses or other elements to hold certain struts of the inflow end of the prosthetic heart valve 200 to constrict those portions of the prosthetic valve from expanding. For example, referring to back to FIG. 1, the secondary distal sheath could capture the terminal inflow struts of stent 202 (e.g. the horse-shoe shaped terminal struts ends) at circumferential locations between the commissure attachment features 216, while the terminal inflow struts directly circumferentially adjacent the commissure attachment features 216 could be free to self-expand. With this configuration, the constraining of the retained terminal inflow struts and the freedom of the non-retained terminal inflow struts will allow the inflow end 230 of the prosthetic heart valve 200 to self-expand into a shape similar to that shown in FIG. 10A mid-deployment. Once the prosthetic heart valve 200 is in the desired alignment, the retained terminal inflow struts may be released from the secondary distal sheath, for example by sliding the secondary distal sheath distally to allow the prosthetic heart valve 200 to fully expand.

Although various individual features for passive commissure-to-commissure alignment are described herein, it should be understood that some of the features may be combinable into a single system. For example, the use of the desired partial-deployment shapes described in connection with FIGS. 10A-B could be combined with any of the delivery device features for commissure-to-commissure alignment described above—particularly those that include rotation of the distal sheath. And still other features could be combined, such as the use of an outer spine similar to that described in connection with FIGS. 4A-B along with an inner spine similar to that described in connection with FIGS. 5A-B.

Further, although much of the disclosure above is described in connection with a transfemoral approach to an aortic valve replacement, the invention is not so limited. For example, any of the embodiments that rely on a particular partial deployment shape may be used in any valve replacement, although it should be understood that the particular partial deployment shape may be tailored to the particular heart valve being replaced. Thus, the partial deployment shape(s) described may be suitable for any of the tricuspid valves (e.g. aortic, pulmonary, or tricuspid valves), while a different shape may be suitable for use in a bicuspid valve replacement (e.g. mitral valve). Similarly, for any of the embodiments that rely on contact between the native leaflets and the delivery device, or high and low velocity blood flow zones to achieve commissure-to-commissure alignment, those embodiments may be suitable for use in any heart valve replacement and via any transcatheter delivery approach. And still further, even for the embodiments that rely upon the particular geometry of the aortic arch to assist with commissure-to-commissure alignment, the concepts described in connection with those embodiments may be modified to achieve similar results in other valve replacement procedures, or even in aortic valve replacement procedures that utilized approaches other than transfemoral delivery.

According to one aspect of the disclosure, a delivery device for a collapsible prosthetic heart valve comprises:
an inner shaft;
an outer shaft;
a distal sheath disposed distal to the outer shaft and about a portion of the inner shaft to form a compartment with the inner shaft, the compartment being sized to receive the prosthetic heart valve, the inner shaft and the distal sheath being movable relative to one another; and
a spine extending along the outer shaft, the spine biasing the outer shaft so that the outer shaft tends to bend in a pre-determined direction; and/or
the spine is positioned along an outer surface of the outer shaft, or extends within a wall of the outer shaft; and/or
the spine includes a plurality of individual plates, each individual plate overlapping a portion of an adjacent plate so that the spine resists bending in a non-preferred direction opposite the pre-determined direction; and/or
the spine is positioned along an interior of the outer shaft; and/or
the spine has a rectangular shape in cross-section and is aligned along a longitudinal axis of the outer shaft, the spine having a first pair of long sides and a second pair of short sides that are shorter than the long sides, the predetermined direction of bend being such that, when the outer shaft has the bend in the predetermined direction, one of the long sides confronts an outer radius of the bend of the outer shaft and the other one of the long sides confronts an inner radius of the bend of the outer shaft; and/or
the prosthetic heart valve includes three prosthetic commissures, one of the three prosthetic commissure being positioned along the outer radius of the bend when the outer shaft has the bend in the predetermined direction and when the prosthetic heart valve is received within the distal sheath; and/or
the spine has a circular shape in cross-section, the spine having a central longitudinal axis that is offset from a central longitudinal axis of the outer shaft, the predetermined direction of bend being such that, when the outer shaft has the bend in the predetermined direction, the spine is positioned closer to an outer radius of the bend of the outer shaft than an inner radius of the bend of the outer shaft; and/or
the prosthetic heart valve includes three prosthetic commissures, one of the three prosthetic commissure being positioned along the outer radius of the bend when the outer shaft has the bend in the predetermined direction and when the prosthetic heart valve is received within the distal sheath; and/or
the spine is formed of a shape-memory material, the shape-memory material configured to assume its set shape upon introduction into a human body.

According to another aspect of the disclosure, a method of implanting a prosthetic heart valve into a native aortic valve of a patient comprises:
loading the prosthetic heart valve into a distal sheath of a delivery device in a collapsed condition, the prosthetic heart valve having three prosthetic commissures;
advancing the distal sheath of the delivery device through an aortic arch of the patient so that an outer shaft of the delivery device includes a bend having an outer radius and an inner radius, one of the three prosthetic commissure confronting the outer radius of the bend during the advancing;
continuing to advance the distal sheath until the distal sheath is adjacent the native aortic valve and the distal sheath is positioned adjacent a native commissure between a right coronary cusp and non-coronary cusp of the patient; and
retracting the distal sheath and expanding the prosthetic heart valve so that the one of the three prosthetic commissure is positioned in rotational alignment with the native commissure; and/or
the outer shaft includes a spine that is either (i) positioned along an outer surface of the outer shaft, or (ii) extends within a wall of the outer shaft, the spine causing the outer shaft of the delivery device to bend during advancement of the distal sheath through the aortic arch so that the spine is positioned along the outer radius of the bend; and/or
the outer shaft includes a spine that includes a plurality of individual plates, each individual plate overlapping a portion of an adjacent plate so that the spine resists bending in a first non-preferred direction and tends to bend in a second preferred direction opposite the non-preferred direction; and/or the outer shaft includes a spine that is positioned along an interior of the outer shaft, the spine having a rectangular shape in cross-section and being aligned along a longitudinal axis of the outer shaft, the spine having a first pair of long sides and a second pair of short sides that are shorter than the long sides, the long sides confronting the inner radius and outer radius of the bend during the advancing of the distal sheath through the aortic arch; and/or the outer shaft includes a spine that is positioned along an interior of the outer shaft, the spine having a circular shape in cross-section, the spine having a central longitudinal axis that is offset from a central longitudinal axis of the outer shaft, the spine being positioned nearer the outer radius of the bend than the inner radius of the bend during the advancing of the distal sheath through the aortic arch; and/or the outer shaft includes a spine formed of a shape-memory material, the spine having a first shape when at a first temperature outside the patient, the spine transitioning to a second set shape after being inserted into the patient and increasing to, or above, a second temperature greater than the first temperature.

According to a further aspect of the disclosure, a delivery device for a collapsible prosthetic heart valve comprises:
an inner shaft;
an outer shaft;
a distal sheath disposed distal to the outer shaft and about a portion of the inner shaft to form a compartment with the inner shaft, the compartment being sized to receive the prosthetic heart valve, the inner shaft and the distal sheath being movable relative to one another, the outer shaft and the distal sheath sharing a central longitudinal axis;
wherein the outer shaft is joined to the distal sheath via a joint so that the distal sheath is capable of rotation about the central longitudinal axis while the outer shaft remains static relative to the central longitudinal axis; and/or
the joint is a rotary bearing; and/or
the rotary bearing is a thrust bearing; and/or
the distal shaft includes a flat protrusion extending a length radially outward therefrom; and/or
the distal sheath has a diameter that is equal to or smaller than the length; and/or
the prosthetic heart valve includes three prosthetic commissures, one of the prosthetic commissures being positioned diametrically opposed the protrusion when the prosthetic heart valve is received within the distal sheath; and/or
the distal shaft includes a triangular protrusion integral with the distal sheath, the protrusion extending away from a central longitudinal axis of the distal sheath; and/or
the protrusion has a length smaller than a diameter of the distal sheath; and/or
the triangular protrusion is configured to be received within a commissural space defined between two adjacent native heart valve leaflets; and/or
the distal sheath includes a fin extending radially outward therefrom, the fin tending to rotate from an area of relatively high blood flow velocity to an area of relatively low blood flow velocity upon exposure to blood flowing across the fin from a distal end of the fin toward a proximal end of the fin; and/or
the distal sheath includes a fin extending radially outward therefrom, the fin tending to rotate from an area of relatively low blood flow velocity to an area of relatively high blood flow velocity upon exposure to blood flowing across the fin from a distal end of the fin toward a proximal end of the fin; and/or
the distal sheath includes a fin extending radially outward therefrom, the fin tending to rotate in a single rotational direction upon exposure to blood flowing across the fin from a distal end of the fin toward a proximal end of the fin; and/or
an inflow end of the prosthetic heart valve is configured to expand to a generally triangular or egg shape in cross-section when the distal sheath is retracted such that the prosthetic heart valve is partially deployed with the inflow end of the prosthetic heart valve being uncovered by the distal sheath and an outflow end of the prosthetic heart valve being covered by the distal sheath; and/or
a plurality of tethers coupled to the prosthetic heart valve, the plurality of tethers configured to constrain the prosthetic heart valve to the generally triangular or egg shape when the prosthetic heart valve is partially deployed; and/or
a plurality of arms extending distally from the distal sheath, the plurality of arms configured to contact the prosthetic heart valve and to constrain the prosthetic heart valve to the generally triangular or egg shape when the prosthetic heart valve is partially deployed; and/or
a secondary distal sheath that is positioned distal to the distal sheath when the prosthetic heart valve is partially deployed, portions of the inflow end of the prosthetic heart valve being received within the secondary distal sheath when the prosthetic heart valve is partially deployed so that the secondary distal sheath is configured to constrain the prosthetic heart valve to the generally triangular or egg shape when the prosthetic heart valve is partially deployed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A delivery device for a collapsible prosthetic heart valve, the delivery device comprising:
an inner shaft;
an outer shaft; and
a distal sheath disposed distal to the outer shaft and about a portion of the inner shaft to form a compartment with the inner shaft, the compartment being sized to receive the prosthetic heart valve, the inner shaft and the distal sheath being movable relative to one another, the outer shaft and the distal sheath sharing a central longitudinal axis;

wherein the outer shaft is joined to the distal sheath via a joint so that the distal sheath is capable of rotation about the central longitudinal axis while the outer shaft remains static relative to the central longitudinal axis, wherein the distal sheath includes a fin extending radially outward therefrom, the fin being configured to rotate from an area of relatively high blood flow velocity to an area of relatively low blood flow velocity upon exposure to blood flowing across the fin from a distal end of the fin toward a proximal end of the fin.

2. The delivery device of claim 1, wherein the joint is a rotary bearing.

3. The delivery device of claim 1, wherein the fin includes a ramped surface.

4. The delivery device of claim 1, wherein a radial distance which the fin extends from the distal sheath increases from the distal end of the fin toward the proximal end of of the fin.

5. The delivery device of claim 1, wherein the fin includes a distal ramped portion at which a radial distance that the fin extends from the distal sheath increases in a distal-to-proximal direction of the fin, and a proximal straight portion positioned proximal to the distal ramped portion, the radial distance that the fin extends from the distal sheath being constant along the proximal straight portion.

6. The delivery device of claim 1, wherein the fin is positioned a spaced distance from a distal tip of the delivery device.

7. The delivery device of claim 1, wherein the fin has a wedge shape, a funnel shape, or a shovel shape.

8. A delivery device for a collapsible prosthetic heart valve, the delivery device comprising:
   an inner shaft;
   an outer shaft; and
   a distal sheath disposed distal to the outer shaft and about a portion of the inner shaft to form a compartment with the inner shaft, the compartment being sized to receive the prosthetic heart valve, the inner shaft and the distal sheath being movable relative to one another, the outer shaft and the distal sheath sharing a central longitudinal axis;

wherein the outer shaft is joined to the distal sheath via a joint so that the distal sheath is capable of rotation about the central longitudinal axis while the outer shaft remains static relative to the central longitudinal axis, wherein the distal sheath includes a fin extending radially outward therefrom, the fin being configured to rotate from an area of relatively low blood flow velocity to an area of relatively high blood flow velocity upon exposure to blood flowing across the fin from a distal end of the fin toward a proximal end of the fin.

9. The delivery device of claim 8, wherein the joint is a rotary bearing.

10. The delivery device of claim 8, wherein the fin has an umbrella shape or an airfoil shape.

11. A delivery device for a collapsible prosthetic heart valve, the delivery device comprising:
    an inner shaft;
    an outer shaft; and
    a distal sheath disposed distal to the outer shaft and about a portion of the inner shaft to form a compartment with the inner shaft, the compartment being sized to receive the prosthetic heart valve, the inner shaft and the distal sheath being movable relative to one another, the outer shaft and the distal sheath sharing a central longitudinal axis;

wherein the outer shaft is joined to the distal sheath via a joint so that the distal sheath is capable of rotation about the central longitudinal axis while the outer shaft remains static relative to the central longitudinal axis, wherein the distal sheath includes a fin extending radially outward therefrom, the fin being configured to rotate in a single rotational direction upon exposure to blood flowing across the fin from a distal end of the fin toward a proximal end of the fin.

12. The delivery device of claim 11, wherein the joint is a rotary bearing.

* * * * *